US012673943B2

(12) United States Patent
Mclaughlin et al.

(10) Patent No.: US 12,673,943 B2
(45) Date of Patent: Jul. 7, 2026

(54) METHOD FOR PREPARING AN ENANTIOMERICALLY ENRICHED FORM OF 2-[2-(2-CHLOROTHIAZOL-5-YL)-2-HYDROXY-ETHYL]SULFANYL-6-HYDROXY-3-METHYL-5-PHENYL-PYRIMIDIN-4-ONE

(71) Applicant: BASF SE, Ludwigshafen (DE)

(72) Inventors: Martin John Mclaughlin, Liestal (CH); Christopher Koradin, Ludwigshafen (DE); Rahul Kaduskar, Navi Mumbai (IN); Harish Shinde, Navi Mumbai (IN); Roland Goetz, Ludwigshafen (DE); Guillaume Michel Jacques Garivet, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 412 days.

(21) Appl. No.: 18/272,913

(22) PCT Filed: Jan. 21, 2022

(86) PCT No.: PCT/EP2022/051354

§ 371 (c)(1),
(2) Date: Jul. 18, 2023

(87) PCT Pub. No.: WO2022/157316

PCT Pub. Date: Jul. 28, 2022

(65) Prior Publication Data

US 2024/0116916 A1 Apr. 11, 2024

(30) Foreign Application Priority Data

Jan. 22, 2021 (EP) .................................... 21153034

(51) Int. Cl.
*C07D 417/12* (2006.01)
*B01J 31/18* (2006.01)

(52) U.S. Cl.
CPC ........ *C07D 417/12* (2013.01); *B01J 31/1805* (2013.01); *C07B 2200/07* (2013.01)

(58) Field of Classification Search
CPC .......................... C07D 417/12; C07B 2200/07
See application file for complete search history.

(56) References Cited

FOREIGN PATENT DOCUMENTS

| | | | |
|---|---|---|---|
| CN | 109970731 | B | 5/2020 |
| EP | 4032878 | A1 | 7/2022 |
| EP | 4032894 | A1 | 7/2022 |
| WO | WO-2014/167084 | A1 | 10/2014 |
| WO | WO-2018/177970 | A1 | 10/2018 |
| WO | WO-2018/197541 | A1 | 11/2018 |
| WO | WO-2018/202654 | A1 | 11/2018 |

OTHER PUBLICATIONS

Chemical Abstracts No. 332383-03-6, indexed in the Registry file on STN CAS Online Apr. 25, 2001. (Year: 2001).*
Chalopin, et al., "Second generation of thiazolylmannosides, FimH antagonists for *E. coli*-induced Crohn's disease", Organic & Biomolecular Chemistry, vol. 14, Issue 16, Mar. 22, 2016, pp. 3913-3925.
International Application No. PCT/EP2022/051354, International Search Report and Written Opinion, mailed Apr. 4, 2022.
European Patent Application No. 21153034.0, Extended European Search Report, mailed May 7, 2021.

* cited by examiner

*Primary Examiner* — Laura L Stockton
(74) *Attorney, Agent, or Firm* — MARSHALL, GERSTEIN & BORUN LLP

(57) ABSTRACT

The present invention relates to a method for preparing 2-[2-(2-chlorothiazol-5-yl)-2-hydroxy-ethyl]sulfanyl-6-hydroxy-3-methyl-5-phenyl-pyrimidin-4-one or a tautomer thereof or enantiomerically enriched forms thereof, to 2-[2-(2-chlorothiazol-5-yl)-2-hydroxy-ethyl]sulfanyl-6-hydroxy-3-methyl-5-phenyl-pyrimidin-4-one or a tautomer thereof or enantiomerically enriched forms thereof, and to the use thereof as intermediate in the preparation of 2,3-dihydrothiazolo[3,2-a]pyrimidinium compounds, specifically of 3-(2-chlorothiazol-5-yl)-8-methyl-7-oxo-6-phenyl-2,3-dihydrothiazolo[3,2-a]pyrimidin-4-ium-5-olate and enantiomerically enriched forms thereof.

26 Claims, No Drawings

METHOD FOR PREPARING AN ENANTIOMERICALLY ENRICHED FORM OF 2-[2-(2-CHLOROTHIAZOL-5-YL)-2-HYDROXY-ETHYL]SULFANYL-6-HYDROXY-3-METHYL-5-PHENYL-PYRIMIDIN-4-ONE

CROSS-REFERENCE TO RELATED APPLICATIONS

This is the U.S. national phase of International Application No. PCT/EP2022/051354, filed Jan. 21, 2022, which claims the benefit of European Patent Application No. 21153034.0, filed Jan. 22, 2021.

The present invention relates to a method for preparing 2-[2-(2-chlorothiazol-5-yl)-2-hydroxy-ethyl]sulfanyl-6-hydroxy-3-methyl-5-phenyl-pyrimidin-4-one of the formula (I) as depicted below or a tautomer thereof or enantiomerically enriched forms thereof, to 2-[2-(2-chlorothiazol-5-yl)-2-hydroxy-ethyl]sulfanyl-6-hydroxy-3-methyl-5-phenyl-pyrimidin-4-one of the formula (I) as depicted below or a tautomer thereof or enantiomerically enriched forms thereof, and to the use thereof as intermediate in the preparation of 2,3-dihydrothiazolo[3,2-a]pyrimidinium compounds, specifically of 3-(2-chlorothiazol-5-yl)-8-methyl-7-oxo-6-phenyl-2,3-dihydrothiazolo[3,2-a]pyrimidin-4-ium-5-olate and enantiomerically enriched forms thereof.

TECHNICAL BACKGROUND

2-[2-(2-Chlorothiazol-5-yl)-2-hydroxy-ethyl]sulfanyl-6-hydroxy-3-methyl-5-phenyl-pyrimidin-4-one (I) (or its tautomer) has been found to be a valuable intermediate in the preparation of 2,3-dihydrothiazolo[3,2-a]pyrimidinium compounds, and more specifically of 3-(2-chlorothiazol-5-yl)-8-methyl-7-oxo-6-phenyl-2,3-dihydrothiazolo[3,2-a]pyrimidin-4-ium-5-olate and enantiomerically enriched forms thereof if 2-[2-(2-chlorothiazol-5-yl)-2-hydroxy-ethyl]sulfanyl-6-hydroxy-3-methyl-5-phenyl-pyrimidin-4-one is used in an enantiomerically enriched form. Said pyriminidium compounds have insecticidal properties and are known, for example, from WO 2018/177970 or WO 2014/167084.

The methods thus far known for the preparation of these pyriminidium compounds are cumbersome and not yet satisfactory.

In WO 2018/177970, WO 2018/197541 and WO 2018/202654, non-racemic 2,3-dihydrothiazolo[3,2-a]pyrimidinium compounds are prepared by reaction of a non-racemic 4-heteroaryl-substituted thiazolidin-2-imine with a 2-substituted malonic acid derivative. In WO 2018/177970 and WO 2018/197541, the non-racemic 4-heteroaryl-substituted thiazolidin-2-imine is in turn prepared by catalytic asymmetric hydrogenation of a 1-heteroaryl-substituted ethanimine carrying in 2-position a leaving group. The resulting amine is then reacted with an isothiocyanate to the thiazolidin-2-imine. The reaction sequence is described in WO 2018/197541 as follows:

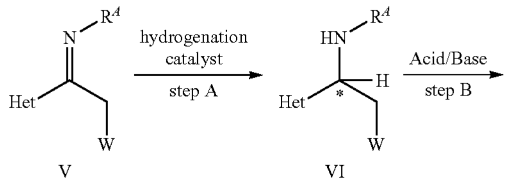

V VI

-continued

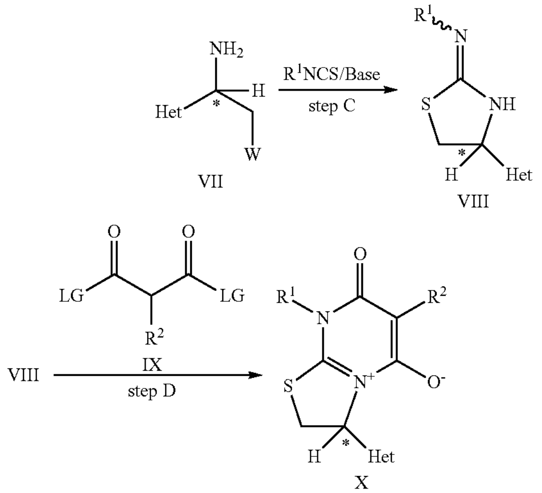

VII VIII X $R^A$ is a sulfanyl or sulfinyl, phosphoroxy, alkoxy or benzyl group; Het is optionally substituted pyridin-3-yl, thiazol-5-yl or pyrimidin-5-yl, W and LG are leaving groups, $R^1$ is a (cyclo)aliphatic group and $R^2$ is 5- or 6-membered carbo- or heterocyclic ring. In WO 2018/177970 the amine VII is obtained via another reaction path from the corresponding sulfinylimine.

WO 2018/177970 and WO 2018/202654 describe a further access to the non-racemic 4-heteroaryl-substituted thiazolidin-2-imine. This is here prepared starting from a heteroarylmethyl ketone, where the methyl group carries a leaving group, conversion of this leaving group into an alkylcarbonyloxy group, hydrolysis of the latter to a hydroxyl group, reaction of the resulting heteroarylhydroxymethyl ketone with a sulfamoyl halide to a 4-heteroaryl-5H-oxathiazole 2,2-dioxide, submission of the latter to a catalytic asymmetric hydrogenation to yield a non-racemic 4-heteroaryloxathiazolidine 2,2-dioxide and reaction thereof with an isothiocyanate to the thiazolidin-2-imine. The reaction sequence is described in WO 2018/202654 as follows:

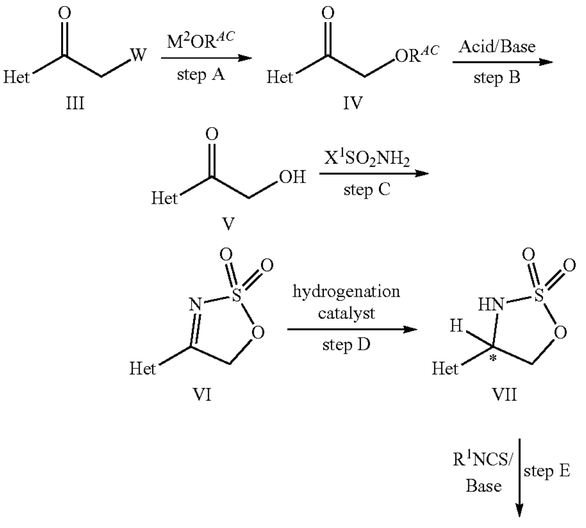

III IV V VI VII

-continued

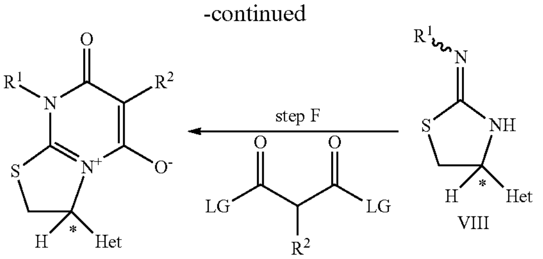

X IX VIII

Het is optionally substituted pyridin-3-yl, thiazol-5-yl or pyrimidin-5-yl, W and LG are leaving groups, $M^2$ is Li, Na, K, Al, Ba, Cs, Ca or Mg, $R^{AC}$ is alkylcarbonyl, $X^1$ is halogen, $R^1$ is a (cyclo)aliphatic group and $R^2$ is 5- or 6-membered carbo- or heterocyclic ring.

These methods are however not very economic. Some reagents are expensive, recycling of some of the reagents which are not or not entirely consumed is difficult, the overall yield is not satisfactory and too many reaction steps are involved.

SUMMARY OF THE INVENTION

It was the object of the present invention to provide an economic process for the preparation of 2-[2-(2-chlorothiazol-5-yl)-2-hydroxy-ethyl]sulfanyl-6-hydroxy-3-methyl-5-phenyl-pyrimidin-4-one and especially a process for the preparation of an enantiomerically enriched form thereof which yields the S or R enantiomer with high selectivity.

The problem is solved by a method for preparing an enantiomerically enriched form of 2-[2-(2-chlorothiazol-5-yl)-2-hydroxy-ethyl]sulfanyl-6-hydroxy-3-methyl-5-phenyl-pyrimidin-4-one of the formula (I):

(I)

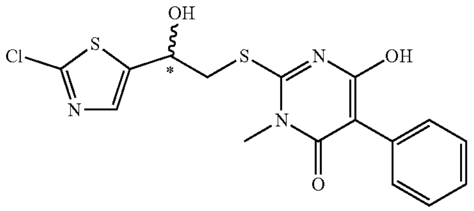

where the asterisk * shows the stereogenic center;

or a tautomer thereof;

which method comprises reducing 2-[2-(2-chlorothiazol-5-yl)-2-oxo-ethyl]sulfanyl-6-hydroxy-3-methyl-5-phenyl-pyrimidin-4-one of the formula 1

1

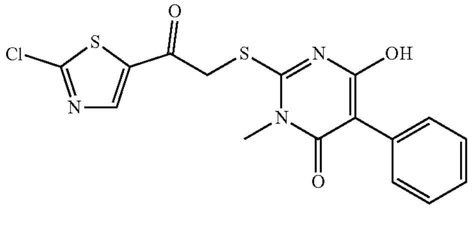

or a tautomer thereof with a reduction agent selected from the group consisting of formic acid HC(=O)OH, formates of the formula HC(=O)$O^-M^+$ and mixtures of formic acid HC(=O)OH and one or more formates of the formula HC(=O)$O^-M^+$, where $M^+$ is a cation equivalent; in the presence of a chiral transition metal catalyst and optionally of a base, where in case that formic acid is used as reduction agent, the reaction is carried out in the presence of a base;

to obtain an enantiomerically enriched form of the pyrimidinone of the formula (I) or of a tautomer thereof.

The invention relates moreover to 2-[2-(2-chlorothiazol-5-yl)-2-hydroxy-ethyl]sulfanyl-6-hydroxy-3-methyl-5-phenyl-pyrimidin-4-one (I)

(I)

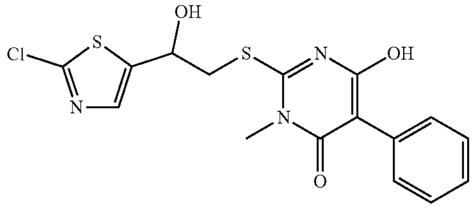

or a tautomer thereof, and to enantiomerically enriched forms thereof. This formula (I) and the formula (I) depicted above in context with the method of the invention are equivalent; the formula (I) depicted in context with the method of the invention shows however more clearly the stereogenic center of the molecule.

The invention relates also to the use of 2-[2-(2-chlorothiazol-5-yl)-2-hydroxy-ethyl]sulfanyl-6-hydroxy-3-methyl-5-phenyl-pyrimidin-4-one (I) or of a tautomer thereof or of enantiomerically enriched forms thereof as intermediate in the preparation of 2,3-dihydrothiazolo[3,2-a]pyrimidinium compounds, and specifically of 3-(2-chlorothiazol-5-yl)-8-methyl-7-oxo-6-phenyl-2,3-dihydrothiazolo[3,2-a]pyrimidin-4-ium-5-olate and enantiomerically enriched forms thereof.

DETAILED DESCRIPTION OF THE INVENTION

Definitions

"Enantiomerically enriched form" of 2-[2-(2-chlorothiazol-5-yl)-2-hydroxy-ethyl]sulfanyl-6-hydroxy-3-methyl-5-phenyl-pyrimidin-4-one of the formula (I) or the compound (I) in enantiomerically enriched form" and similar terms denote a non-racemic compound (I) in which either the S enantiomer or the R enantiomer predominates or is even present as only stereoisomer. The compound (I) has a single stereogenic center which is at the aliphatic carbon atom carrying the OH group and marked with an asterisk.

$M^+$ is a cation equivalent. It stands for a metal cation or an ammonium cation (ammonium in this case stands for both the ammonium cation $NH_4^+$ in the proper sense, but also for substituted ammonium cations). In case of cations with double or triple charge, the cation equivalent can be depicted as $(M^{n+})_{1/n}$, where n is the charge number.

Formate in the context of the present invention is a salt of formic acid (HC(=O)$O^-M^+$, where $M^+$ is a cation equivalent). The term can also stand for the anion (HC(=O)$O^-$) of formic acid. In context of the present invention, the term does however not denote the esters, unless explicitly mentioned otherwise.

The organic moieties mentioned below are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine, chlorine or bromine.

The term "alkyl" as used herein and in the alkyl moieties of alkoxy refers to saturated straight-chain (linear) or branched hydrocarbon radicals having 1 to 3 ("$C_1$-$C_3$-alkyl"), 1 to 4 ("$C_1$-$C_4$-alkyl") or 1 to 6 ("$C_1$-$C_6$-alkyl") carbon atoms. $C_1$-$C_3$-Alkyl denotes a saturated linear or branched aliphatic radical with 1 to 3 carbon atoms. Examples are methyl, ethyl, n-propyl or isopropyl. $C_1$-$C_4$-Alkyl denotes a saturated linear or branched aliphatic radical with 1 to 4 carbon atoms. Examples are methyl, ethyl, n-propyl, isopropyl, n-butyl, sec-butyl, isobutyl and tert-butyl. $C_1$-$C_6$-Alkyl denotes a saturated linear or branched aliphatic radical with 1 to 6 carbon atoms. Examples are, in addition to those mentioned for $C_1$-$C_4$-alkyl, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl.

The term "$C_1$-$C_4$-haloalkyl" as used herein, which can also be expressed as "alkyl which is partially or fully halogenated", refers to straight-chain or branched alkyl groups having 1 to 4 carbon atoms (as mentioned above), where some or all of the hydrogen atoms in these groups are replaced by halogen atoms as mentioned above. Examples are chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl. $C_1$-$C_3$-haloalkyl is additionally, for example, 1-fluoropropyl, 2-fluoropropyl, 3-fluoropropyl, 1,1-difluoropropyl, 2,2-difluoropropyl, 1,2-difluoropropyl, 3,3-difluoropropyl, 3,3,3-trifluoropropyl, heptafluoropropyl, 1,1,1-trifluoroprop-2-yl, 3-chloropropyl, 4-chlorobutyl and the like.

The term "$C_3$-$C_6$-cycloalkyl" as used herein refers to monocyclic saturated hydrocarbon radicals having 3 to 6 carbon atoms as (only) ring members. Examples are cyclopropyl, cyclobutyl, cyclopentyl and cyclohexyl.

The term $C_6$-$C_{10}$-bicycloalkyl refers to bicyclic bridged saturated hydrocarbon radicals containing 6 to 10 carbon atoms as (only) ring members. Examples are bicyclo[2.2.1]heptyl, bicyclo[3.1.1]heptyl, bicyclo[2.2.2]octyl, bicyclo[3.2.1]octyl and the like. Examples for $C_6$-$C_{10}$-bicycloalkyl substituted by alkyl and/or oxo are 7,7-dimethyl-bicyclo[2.2.1]hept-1-yl and 7,7-dimethyl-2-oxo-bicyclo[2.2.1]hept-1-yl.

The term $C_6$-$C_{10}$-bicycloalkyl-$C_1$-$C_3$-alkyl refers to a straight-chain or branched alkyl group having 1 to 3 carbon atoms, as defined above, where one hydrogen atom is replaced by a $C_6$-$C_{10}$-bicycloalkyl group, as defined above.

The term "$C_1$-$C_4$-alkoxy" refers to a $C_1$-$C_4$-alkyl group, as defined above, attached via an oxygen atom to the remainder of the molecule. Examples are methoxy, ethoxy, n-propoxy, 1-methylethoxy (isopropoxy), n-butoxy, 1-methylpropoxy (sec-butoxy), 2-methylpropoxy (isobutoxy) or 1,1-dimethylethoxy (tert-butoxy).

The term "$C_1$-$C_4$-alkoxy-$C_1$-$C_4$-alkyl" refers to a straight-chain or branched alkyl group having 1 to 4 carbon atoms, as defined above, where one hydrogen atom is replaced by a $C_1$-$C_4$-alkoxy group, as defined above. Examples are methoxymethyl, ethoxymethyl, propoxymethyl, isopropoxymethyl, n-butoxymethyl, sec-butoxymethyl, isobutoxymethyl, tert-butoxymethyl, 1-methoxyethyl, 1-ethoxyethyl, 1-propoxyethyl, 1-isopropoxyethyl, 1-n-butoxyethyl, 1-sec-butoxyethyl, 1-isobutoxyethyl, 1-tert-butoxyethyl, 2-methoxyethyl, 2-ethoxyethyl, 2-propoxyethyl, 2-isopropoxyethyl, 2-n-butoxyethyl, 2-sec-butoxyethyl, 2-isobutoxyethyl, 2-tert-butoxyethyl, 1-methoxypropyl, 1-ethoxypropyl, 1-propoxypropyl, 1-isopropoxypropyl, 1-n-butoxypropyl, 1-sec-butoxypropyl, 1-isobutoxypropyl, 1-tert-butoxypropyl, 2-methoxypropyl, 2-ethoxypropyl, 2-propoxypropyl, 2-isopropoxypropyl, 2-n-butoxypropyl, 2-sec-butoxypropyl, 2-isobutoxypropyl, 2-tert-butoxypropyl, 3-methoxypropyl, 3-ethoxypropyl, 3-propoxypropyl, 3-isopropoxypropyl, 3-n-butoxypropyl, 3-sec-butoxypropyl, 3-isobutoxypropyl, 3-tert-butoxypropyl and the like.

"Phenyl-$C_1$-$C_3$-alkyl" refers to straight-chain or branched alkyl groups having 1 to 3 carbon atoms (as mentioned above), where one hydrogen atom is replaced by a phenyl ring (in other words: a phenyl group bound via a $C_1$-$C_3$-alkylene linker to the remainder of the molecule).

Alkylene is a linear or branched divalent alkanediyl radical. $C_1$-$C_3$-Alkylene is a linear or branched divalent alkyl radical having 1, 2 or 3 carbon atoms. Examples are $-CH_2-$, $-CH_2CH_2-$, $-CH(CH_3)-$, $-CH_2CH_2CH_2-$, $-CH(CH_3)CH_2-$, $-CH_2CH(CH_3)-$ and $-C(CH_3)_2-$. $C_2$-$C_6$-Alkylene is a linear or branched divalent alkyl radical having 2, 3, 4, 5 or 6 carbon atoms. Examples are $-CH_2CH_2-$, $-CH(CH_3)-$, $-CH_2CH_2CH_2-$, $-CH(CH_3)CH_2-$, $-CH_2CH(CH_3)-$, $-C(CH_3)_2-$, $-CH_2CH_2CH_2CH_2-$, $-CH(CH_3)CH_2CH_2-$, $-CH_2CH_2CH(CH_3)-$, $-C(CH_3)_2CH_2-$, $-CH_2C(CH_3)_2-$, $-(CH_2)_5-$, $-(CH_2)_6-$, and positional isomers thereof.

Linear $C_3$-$C_6$-alkylene is $-(CH_2)_3-$, $-(CH_2)_4-$, $-(CH_2)_5-$ or $-(CH_2)_6-$.

5- or 6-membered saturated heterocyclic rings containing one nitrogen atom as ring member and optionally one further heteroatom selected from N and O as ring member are for example pyrrolidine, pyrazolidine, imidazolidine, oxazolidine, isoxazolidine, piperidine, piperazine, or morpholine.

Oxo is $=O$; i.e. the substituent "oxo" replaces a $CH_2$ group by a $C(=O)$ group.

Group VIII metal catalysts refer to catalysts having a metal from group VIII of the periodic system of elements as central metal. Group VIII relates to the IUPAC group definition valid before 1985 and corresponds to groups 8, 9 and 10 of the current IU-PAC group designation.

The compound (I) can be present as a tautomer thereof or as a mixture of different tautomeric forms. An example for a tautomeric form of the compound of the formula (I) as depicted above is the following formula:

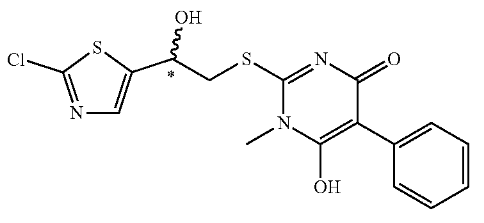 [SMILES: Cn1c(SCC(O)c2cnc(Cl)s2)nc(=O)c(-c2ccccc2)c1O]

Mixtures of different tautomeric forms are for example mixtures of this tautomer the tautomer depicted above as formula (I).

Also compound 1 can be present as a tautomer thereof or as a mixture of different tautomeric forms. An example for a tautomeric form of the compound of the formula 1 as depicted above is the following formula:

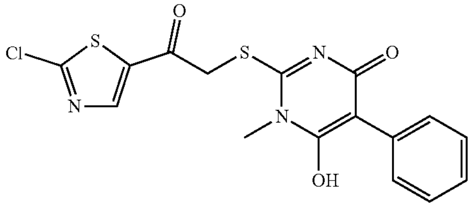 [SMILES: Cn1c(SCC(=O)c2cnc(Cl)s2)nc(=O)c(-c2ccccc2)c1O]

Mixtures of different tautomeric forms are for example mixtures of this tautomer the tautomer depicted above as formula 1.

For the sake of simplicity, in the following only compounds (I) and 1 are mentioned. Nevertheless, all embodiments also relate to their tautomers and mixtures of different tautomeric forms thereof.

Embodiments (E.x) of the Invention

General and preferred embodiments E.x are summarized in the following, non-exhaustive list. Further preferred embodiments become apparent from the paragraphs following this list.

E.1. A method for preparing an enantiomerically enriched form of 2-[2-(2-chlorothiazol-5-yl)-2-hydroxy-ethyl]sulfanyl-6-hydroxy-3-methyl-5-phenyl-pyrimidin-4-one of the formula (I):

(I)

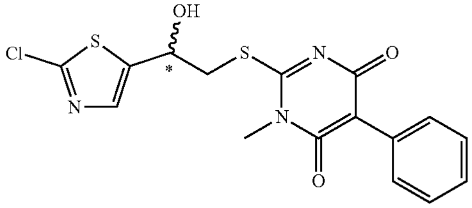

where the asterisk * shows the stereogenic center;

which method comprises reducing 2-[2-(2-chlorothiazol-5-yl)-2-oxo-ethyl]sulfanyl-6-hydroxy-3-methyl-5-phenyl-pyrimidin-4-one of the formula 1

1

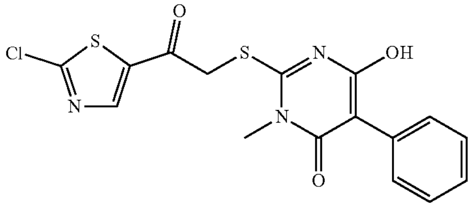

with a reduction agent selected from the group consisting of formic acid HC(═O)OH, formates of the formula $HC(=O)O^-M^+$ and mixtures of formic acid HC(═O)OH and one or more formates of the formula $HC(=O)O^-M^+$, where $M^+$ is a cation equivalent; in the presence of a chiral transition metal catalyst and optionally of a base, where in case that formic acid is used as reduction agent, the reaction is carried out in the presence of a base;

to obtain an enantiomerically enriched form of the pyrimidinone of the formula (I).

E.2. The method according to embodiment E.1, where $M^+$ is selected from the group consisting of alkali metal cations, ammonium cations of the formula $[NHR^1R^2R^3]^+$, where $R^1$, $R^2$ and $R^3$, independently of each other, are selected from the group consisting of hydrogen, $C_1$-$C_6$-alkyl, $C_3$-$C_6$-cycloalkyl, $C_1$-$C_4$-alkoxy and $C_1$-$C_4$-alkoxy-$C_1$-$C_4$-alkyl, protonated diamines of the formula $NR^1R^2$-A-$NR^3R^4$, where $R^1$, $R^2$, $R^3$ and $R^4$, independently of each other, are selected from the group consisting of hydrogen, $C_1$-$C_6$-alkyl, $C_3$-$C_6$-cycloalkyl, $C_1$-$C_4$-alkoxy and $C_1$-$C_4$-alkoxy-$C_1$-$C_4$-alkyl, and A is $(CH_2)_2$ or $(CH_2)_3$; and protonated 5- or 6-membered saturated heterocyclic rings containing one nitrogen atom as ring member and optionally one further heteroatom selected from N and O as ring member, where the ring may carry 1 to 6 $C_1$-$C_4$-alkyl groups and/or 1 or 2 OH groups.

E.3. The method according to embodiment E.2, where $M^+$ is selected from the group consisting of $Li^+$, $Na^+$, $K^+$, $Cs^+$, $NH_4^+$, $[NH_2(C_2H_5)_2]^+$, $[NH(C_2H_5)_3]^+$, $[NH(CH_2CH_2CH_2CH_3)_3]^+$, $[NH(C_2H_5)(CH(CH_3)_2]^+$, $[NH(CH_3)_2(CH(CH_3)]^+$, $[NH_2(C_2H_5)(C(CH_3)_3]^+$, $[NH_2(CH(CH_3)_2)(C(CH_3)_3]^+$, $[NH_2(C_2H_4OCH_3)(CH_3)]^+$, $[NH(cyclohexyl)_2(CH_3)]^+$, $[NH(cyclohexyl)(CH_3)_2]^+$, protonated N,N,N',N'-tetramethylethylenediamine, protonated N,N,N',N'-tetramethylpropylene-1,3-diamine, protonated piperdine, protonated N-methylpiperidine, protonated 2,2,6,6-tetramethylpiperidine, protonated N-methyl-2,6,6-tetramethylpiperidine, protonated N-methyl-4-hydroxy-2,2,6,6-tetramethylpiperidine, protonated morpholine, and protonated N-methylmorpholine.

E.4. The method according to embodiment E.2, where $M^+$ is selected from the group consisting of alkali metal cations and ammonium cations of the formula $[NHR^1R^2R^3]^+$, where $R^1$, $R^2$ and $R^3$, independently of each other, are selected from the group consisting of hydrogen and $C_1$-$C_6$-alkyl, where preferably at least one, preferably at least two of $R^1$, $R^2$ and $R^3$ are $C_1$-$C_6$-alkyl.

E.5. The method according to any of embodiments E.3 or E.4, where $M^+$ is selected from the group consisting of $Na^+$, $K^+$, $[NH(C_2H_6)_3]^+$, $[NH(CH_2CH_2CH_2CH_3)_3]^+$ and $[NH(C_2H_6)(CH(CH_3)_2]^+$.

E.6. The method according to any of embodiment E.3 to E.5, where $M^+$ is selected from the group consisting of $[NH(C_2H_6)_3]^+$, $[NH(CH_2CH_2CH_2CH_3)_3]^+$ and $[NH(C_2H_6)(CH(CH_3)_2]^+$.

E.7. The method according to any of embodiment E.3 to E.5, where $M^+$ is $Na^+$ or $K^+$.

E.8. The method according to any of the preceding embodiments, where the base is selected from the group consisting of alkali metal hydroxides, amines of the formula $NR^1R^2R^3$, where $R^1$, $R^2$ and $R^3$, independently of each other, are selected from the group consisting of hydrogen, $C_1$-$C_6$-alkyl, $C_3$-$C_6$-cycloalkyl, $C_1$-$C_4$-alkoxy and $C_1$-$C_4$-alkoxy-$C_1$-$C_4$-alkyl, where at least one of $R^1$, $R^2$ and $R^3$ is not hydrogen; diamines of the formula $NR^1R^2$-A-$NR^3R^4$, where $R^1$, $R^2$, $R^3$ and $R^4$, independently of each other, are selected from the group consisting of hydrogen, $C_1$-$C_6$-alkyl, $C_3$-$C_6$-cycloalkyl, $C_1$-$C_4$-alkoxy and $C_1$-$C_4$-alkoxy-$C_1$-$C_4$-alkyl, and A is $(CH_2)_2$ or $(CH_2)_3$; and a 5- or 6-membered saturated heterocyclic ring containing one nitrogen atom as ring member and optionally one further heteroatom selected from N and O as ring member, where the ring may carry 1 to 6 $C_1$-$C_4$-alkyl groups and/or 1 or 2 OH groups.

E.9. The method according to embodiment E.8, where the base is selected from the group consisting of LiOH, NaOH, KOH, diethylamine, triethylamine, tributylamine, diisopropylethylamine, dimethylisopropylamine, ethyl-tert-butylamine, isopropyl-tert-butylamine, (2-methoxyethyl)methylamine, N,N-dicyclohexylmethylamine, N-cyclohexyldimethylamine, N,N,N',N'-tetramethylethylenediamine, N,N,N',N'-tetramethylpropylene-1,3-diamine, piperdine, N-methylpiperidine, 2,2,6,6-tetramethylpiperidine, N-methyl-2,6,6-tetramethylpiperidine, N-methyl-4-hydroxy-2,2,6,6-tetramethylpiperidine, morpholine and N-methylmorpholine, where the bases can be used in supported from (i.e. on a support material).

E.10. The method according to embodiment E.8, where the base is selected from the group consisting of amines of the formula $NR^1R^2R^3$, where $R^1$, $R^2$ and $R^3$, independently of each other, are selected from the group consisting of hydrogen and $C_1$-$C_6$-alkyl, where at least one of $R^1$, $R^2$ and $R^3$ is $C_1$-$C_6$-alkyl.

E.11. The method according to any of embodiments E.9 or E.10, where the base is selected from the group consisting of triethylamine, tributylamine and diisopropylethylamine.

E.12. The method according to embodiment E.9, where the base is selected from the group consisting of NaOH and KOH.

E.13. The method according to any of the preceding embodiments, where formic acid is used as reduction agent, where formic acid and the base are used in a molar ratio of from 100:1 to 1:10.

E.14. The method according to embodiment E.13, where formic acid and the base are used in a molar ratio of from 10:1 to 1:5.

E.15. The method according to embodiment E.14, where formic acid and the base are used in a molar ratio of from 10:1 to 1:2.

E.16. The method according to embodiment E.15, where formic acid and the base are used in a molar ratio of from 5:1 to 1:5, E.17. The method according to embodiment E.16, where formic acid and the base are used in a molar ratio of from 5:1 to 1:1.

E.18. The method according to any of the preceding embodiments, where the compound 1 and the reduction agent are used in a molar ratio of from 1:1 to 1:10.

E.19. The method according to embodiment E.18, where the compound 1 and the reduction agent are used in a molar ratio of from 1:1 to 1:5.

E.20. The method according to any of the preceding embodiments, where in the chiral transition metal catalyst one or more chiral ligands are coordinatively bound to the central transition metal.

E.21. The method according to any of the preceding embodiments, where the chiral transition metal catalyst is selected from group VIII metal catalysts.

E.22. The method according to embodiment E.21, where the chiral transition metal catalyst is selected from group 8 and 9 metal catalysts.

E.23. The method according to embodiment E.22, where the chiral transition metal catalyst is selected from Ru, Rh and Ir catalysts E.24. The method according to embodiment E.23, where the chiral transition metal catalyst is selected from Rh and Ir catalysts.

E.25. The method according to any of the preceding embodiments, where the chiral transition metal catalyst, calculated on the basis of the transition metal content, is used in an amount of from 0.01 to 10 mol %, relative to 1 mol of the compound 1.

E.26. The method according to embodiment E.25, where the chiral transition metal catalyst, calculated on the basis of the transition metal content, is used in an amount of from 0.05 to 5 mol-%, relative to 1 mol of the compound 1.

E.27. The method according to embodiment E.26, where the chiral transition metal catalyst, calculated on the basis of the transition metal content, is used in an amount of from 0.1 to 5 mol-%, relative to 1 mol of the compound 1.

E.28. The method according to embodiment E.27, where the chiral transition metal catalyst, calculated on the basis of the transition metal content, is used in an amount of from 0.1 to 2 mol-%, relative to 1 mol of the compound 1.

E.29. The method according to any of the preceding embodiments, where the chiral transition metal catalyst is either preformed and contains one or more chiral ligands coordinated to the transition metal; or is formed in situ by reaction of a transition metal precursor compound and one or more chiral ligands.

E.30. The method according to embodiment E.29, where the chiral ligands are selected from the group consisting of bidentate amine-based chiral ligands.

E.31. The method according to embodiment E.30, where the chiral ligands are selected from the group consisting of chiral 1,2-diphenyl-ethylene-1,2-diamines, 1,2-cyclohexanediamines, and 1,2-bis(methylamino)cyclohexanes.

E.32. The method according to embodiment E.31, where the chiral ligands are selected from the group consisting of chiral 1,2-diphenyl-ethylene-1,2-diamines.

E.33. The method according to embodiment E.32, where the chiral ligands are selected from the group consisting of the chiral forms of 1,2-diphenyl-ethylene-1,2-diamines of the formula (II)

(II)

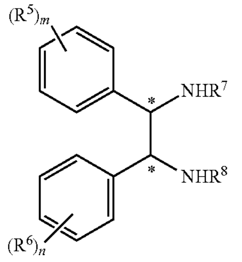

where the asterisk shows the stereogenic centers;

$R^5$ and $R^6$, independently of each other, are selected from the group consisting of OH, halogen, $C_1$-$C_4$-alkyl and $C_1$-$C_4$-alkoxy;

$R^7$ and $R^8$, independently of each other, are selected from the group consisting of hydrogen, $C_1$-$C_4$-alkyl, -L-phenyl, where the phenyl ring may carry 1, 2, 3, 4 or 5 substituents selected from the group consisting of $C_1$-$C_4$-alkyl, $C_1$-$C_4$-haloalkyl and $C_1$-$C_4$-alkoxy; and $SO_2R^9$;

L is a linker selected from the group consisting of $C_2$-$C_6$-alkylene, $C_1$-$C_3$-alkylene-O—$(CH_2)_p$, where p is 0, 1 or 2; and $C_1$-$C_3$-alkylene-(1,2-phenylene)-$(CH_2)_r$, where r is 0, 1 or 2;

$R^9$ is selected from the group consisting of $C_1$-$C_4$-alkyl, $C_1$-$C_4$-haloalkyl, phenyl, phenyl-$C_1$-$C_3$-alkyl, where phenyl in the two aforementioned radicals may carry 1, 2, 3, 4 or 5 substituents selected from the group consisting of halogen, $C_1$-$C_4$-alkyl, $C_1$-$C_4$-haloalkyl and $C_1$-$C_4$-alkoxy; naphthyl, $C_6$-$C_{10}$-bicycloalkyl-$C_1$-$C_3$-alkyl, where the bicycloalkyl ring may be substituted by 1, 2, 3, 4 or 5 substituents selected from the group consisting of $C_1$-$C_4$-alkyl and oxo; and $NR^{10}R^{11}$;

$R^{10}$ is hydrogen or $C_1$-$C_4$-alkyl;

$R^{11}$ is phenyl-$C_1$-$C_3$-alkyl, where the phenyl ring may carry 1, 2, 3, 4 or 5 substituents selected from the group consisting of halogen, $C_1$-$C_4$-alkyl, $C_1$-$C_4$-haloalkyl and $C_1$-$C_4$-alkoxy; and m and n, independently of each other, are 0, 1, 2, 3, 4 or 5.

E.34. The method according to embodiment E.33, where in compounds (II)

$R^5$ and $R^6$ are $C_1$-$C_4$-alkoxy;

one of $R^7$ and $R^8$ is selected from the group consisting of hydrogen, $C_1$-$C_4$-alkyl and -L-phenyl, where phenyl may carry 1, 2, 3, 4 or 5 substituents selected from the group consisting of $C_1$-$C_4$-alkyl, $C_1$-$C_4$-haloalkyl and $C_1$-$C_4$-alkoxy; and the other of $R^7$ and $R^8$ is selected from the group consisting of hydrogen and $SO_2R^9$;

L is a linker selected from the group consisting of linear $C_3$-$C_6$-alkylene, $(CH_2)_o$—O—$(CH_2)_p$, where p and o are independently 1 or 2; and $(CH_2)_q$—(1,2-phenylene)-$(CH_2)_r$, where q and r are independently 0, 1 or 2, where at least one of q and r is not 0;

$R^9$ is selected from the group consisting of $C_1$-$C_4$-alkyl, $C_1$-$C_4$-haloalkyl, phenyl which may carry 1, 2, 3, 4 or 5 substituents selected from the group consisting of halogen, $C_1$-$C_4$-alkyl, $C_1$-$C_4$-haloalkyl and $C_1$-$C_4$-alkoxy; $C_7$-bicycloalkyl-methyl, where the bicycloalkyl ring may be substituted by 1, 2 or 3 substituents selected from the group consisting of $C_1$-$C_4$-alkyl and oxo; and $NR^{10}R^{11}$;

$R^{10}$ is hydrogen or $C_1$-$C_4$-alkyl;

$R^{11}$ is phenyl-$(CH_2)_s$-alkyl, where s is 2 or 3 and where the phenyl ring may carry 1, 2, 3, 4 or 5 substituents selected from the group consisting of halogen, $C_1$-$C_4$-alkyl, $C_1$-$C_4$-haloalkyl and $C_1$-$C_4$-alkoxy; and m and n are both 0 or are both 1, and are preferably both 0.

E.35. The method according to any of embodiments E.33 or E.34, where the chiral ligands are selected from the group consisting of the (1R,2R) or (1S,2S) forms of DPEN, TsDPEN, $CF_3$TsDPEN, MsDPEN, MeMsDPEN, MeTsDPEN, FsDPEN, TripsMesitylDPEN, CsDPEN, MesitylDPEN, RsDPEN, TsDiOMeDPEN and of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are O.

E.36. The method according to embodiment 35, where the chiral ligands are selected from the group consisting of the (1R,2R) or (1S,2S) forms of TsDPEN, $CF_3$TsDPEN, MsDPEN, MeMsDPEN, MeTsDPEN, CsDPEN, MesitylDPEN, RsDPEN, TsDiOMeDPEN and of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0.

E.37. The method according to embodiment 36, where the chiral ligands are selected from the group consisting of the (1R,2R) or (1S,2S) forms of TsDPEN, $CF_3$TsDPEN, MsDPEN, MeMsDPEN, MeTsDPEN, CsDPEN, MesitylDPEN, RsDPEN, TsDiOMeDPEN and of a compound of the formula (II), wherein $R^7$ is $SO_2R^9$, where $R^9$ is $C_1$-$C^4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl; and m and n are 0.

E.38. The method according to embodiment E.35, where the chiral transition metal catalysts are catalysts containing Ru, Rh or Ir as central metal and at least one ligand selected from the group consisting of the (1R, 2R) or (1S,2S) forms of DPEN, TsDPEN, $CF_3$TsDPEN, MsDPEN, MeMsDPEN, MeTsDPEN, FsDPEN, TripsMesitylDPEN, CsDPEN, MesitylDPEN, RsDPEN, TsDiOMeDPEN and of a compound of the formula (II), wherein $R^7$ is $SO_2R^9$, where $R^9$ is $C_1$-$C^4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0.

E.39. The method according to embodiment E.38, where the chiral transition metal catalysts are catalysts containing Ru, Rh or Ir as central metal and at least one ligand selected from the group consisting of the (1R, 2R) or (1S,2S) forms of TsDPEN, $CF_3$TsDPEN, MsDPEN, MeMsDPEN, MeTsDPEN, CsDPEN, MesitylDPEN, RsDPEN, TsDiOMeDPEN and of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0.

E.40. The method according to embodiment E.39, where the chiral transition metal catalysts are catalysts containing Ru, Rh or Ir as central metal and at least one ligand selected from the group consisting of the (1R, 2R) or (1S,2S) forms of TsDPEN, $CF_3$TsDPEN, MsDPEN, MeMsDPEN, MeTsDPEN, CsDPEN, MesitylDPEN, RsDPEN, TsDiOMeDPEN and of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl; and m and n are 0.

E.41. The method according to embodiment E.38, where the chiral transition metal catalysts are catalysts containing Ru, Rh or Ir as central metal and at least one ligand selected from the group consisting of the (1R, 2R) or (1S,2S) forms of DPEN, TsDPEN, $CF_3$TsDPEN, MsDPEN, MeMsDPEN, MeTsDPEN, FsDPEN, TripsMesitylDPEN, CsDPEN, MesitylDPEN, RsDPEN and TsDiOMeDPEN; or are a catalyst containing Ru as central metal and at least one ligand selected from the (1R,2R) or (1S,2S) forms of the compounds of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0.

E.42. The method according to embodiment E.41, where the chiral transition metal catalysts are catalysts containing Ru, Rh or Ir as central metal and at least one ligand selected from the group consisting of the (1R, 2R) or (1S,2S) forms of TsDPEN, $CF_3$TsDPEN, MsDPEN, MeMsDPEN, MeTsDPEN, CsDPEN, MesitylDPEN, RsDPEN and TsDiOMeDPEN; or are a catalyst of the following formula

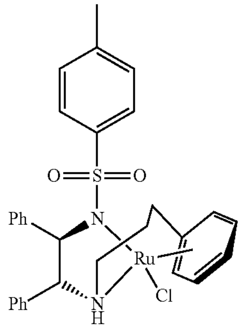

or

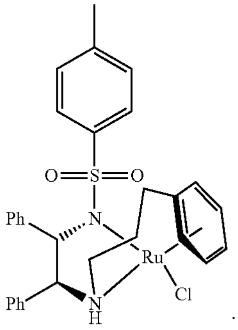

.

E.43. The method according to any of embodiments E.33 to E.42, where in case that none of $R^7$ and $R^8$ is -L-phenyl or $SO_2R^9$ with $R^9$ being phenyl-$C_1$-$C_3$-alkyl or $NR^{10}R^{11}$, the catalyst contains additionally a ligand selected from aromatic rings.

E.44. The method according to embodiment E.43, where the aromatic rings are selected from the group consisting of Cp, Cp*, benzene, p-cymene, mesitylene and hexamethylbenzene.

E.45. The method according to embodiment E.44 where the aromatic rings are selected from the group consisting of Cp*, benzene, p-cymene, mesitylene and hexamethylbenzene, E.46. The method according to embodiment E.45, where the aromatic rings are selected from the group consisting of Cp*, p-cymene and mesitylene.

E.47. The method according to embodiment E.46, where the central metal is Rh or Ir and the aromatic ring is Cp*; or the central metal is Ru and the aromatic ring is p-cymene or mesitylene.

E.48. The method according to any of the preceding embodiments, where the chiral transition metal catalyst additionally contains one or two halogen or sulfonate ligands.

E.49. The method according to embodiment E.48, where chiral transition metal catalyst additionally contains one or two halogen ligands.

E.50. The method according to embodiment E.49, where chiral transition metal catalyst additionally contains one or two, preferably one, Cl ligands.

E.51. The method according to any of the preceding embodiments, for preparing 2-[(2S)-2-(2-chlorothiazol-5-yl)-2-hydroxy-ethyl]sulfanyl-6-hydroxy-3-methyl-5-phenyl-pyrimidin-4-one of the formula (I-S)

(I-S)

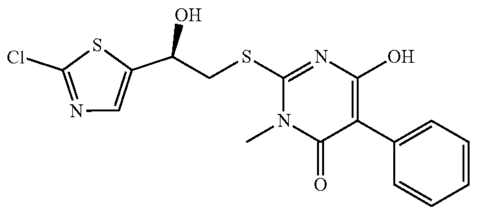

in an enantiomeric excess of at least 55% ee.

E.52. The method according to embodiment E.51, for preparing 2-[(2S)-2-(2-chlorothiazol-5-yl)-2-hydroxy-ethyl]sulfanyl-6-hydroxy-3-methyl-5-phenyl-pyrimidin-4-one of the formula (I-S) in an enantiomeric excess of at least 60% ee.

E.53. The method according to embodiment E.52, for preparing 2-[(2S)-2-(2-chlorothiazol-5-yl)-2-hydroxy-ethyl]sulfanyl-6-hydroxy-3-methyl-5-phenyl-pyrimidin-4-one of the formula (I-S) in an enantiomeric excess of at least 70% ee.

E.54. The method according to embodiment E.53, for preparing 2-[(2S)-2-(2-chlorothiazol-5-yl)-2-hydroxy-ethyl]sulfanyl-6-hydroxy-3-methyl-5-phenyl-pyrimidin-4-one of the formula (I-S) in an enantiomeric excess of at least 80% ee.

E.55. The method according to embodiment E.54, for preparing 2-[(2S)-2-(2-chlorothiazol-5-yl)-2-hydroxy-ethyl]sulfanyl-6-hydroxy-3-methyl-5-phenyl-pyrimidin-4-one of the formula (I-S) in an enantiomeric excess of at least 90% ee.

E.56. The method according to any of embodiments E.51 to E.55, where the chiral transition metal catalyst comprises a chiral ligand selected from the group consisting of (1S,2S)-DPEN, (1S,2S)-TsDPEN, (1S, 2S)—$CF_3$TsDPEN, (1S,2S)-MsDPEN, (1S,2S)-MeMsDPEN, (1S,2S)-MeTsDPEN, (1S,2S)-FsDPEN, (1S,2S)-TripsMesitylDPEN, (1S,2S)-CsDPEN, (1S, 2S)-MesitylDPEN, (1S,2S)-RsDPEN, (1S,2S)-TsDiOMeDPEN and the (1S,2S) form of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0.

E.57. The method according to embodiment E.56, where the chiral transition metal catalyst comprises a chiral ligand selected from the group consisting of (1S,2S)-TsDPEN, (1S,2S)—$CF_3$TsDPEN, (1S,2S)-MsDPEN, (1S,2S)-MeMsDPEN, (1S,2S)-MeTsDPEN, (1S,2S)-CsDPEN, (1S,2S)-MesitylDPEN, (1S,2S)-RsDPEN, (1S,2S)-TsDiOMeDPEN and the (1S,2S) form of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0.

E.58. The method according to embodiment E.57, where the chiral transition metal catalyst comprises a chiral ligand selected from the group consisting of (1S,2S)-TsDPEN, (1S,2S)-$CF_3$TsDPEN, (1S,2S)-MsDPEN, (1S,2S)-MeMsDPEN, (1S,2S)-MeTsDPEN, (1S,2S)-CsDPEN, (1S,2S)-MesitylDPEN, (1S,2S)-RsDPEN, (1S,2S)-TsDiOMeDPEN and the (1S,2S) form of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl; and m and n are 0.

E.59. The method according to any of embodiments E.51 to E.56, where the chiral transition metal catalyst comprises as central metal Ru, Rh or Ir, and comprises a chiral ligand selected from the group consisting of (1S,2S)-DPEN, (1S,2S)-TsDPEN, (1S,2S)—$CF_3$TsDPEN, (1S,2S)-MsDPEN, (1S,2S)-MeMsDPEN, (1S,2S)-MeTsDPEN, (1S,2S)-FsDPEN, (1S,2S)-TripsMesitylDPEN, (1S,2S)-CsDPEN, (1S,2S)-MesitylDPEN, (1S,2S)-RsDPEN, (1S,2S)-TsDiOMeDPEN and the (1S,2S) form of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0.

E.60. The method according to embodiment E.59, where the chiral transition metal catalyst comprises as central metal Ru, Rh or Ir, and comprises a chiral ligand selected from the group consisting of (1S,2S)-TsDPEN, (1S,2S)-$CF_3$TsDPEN, (1S,2S)-MsDPEN, (1S,2S)-MeMsDPEN, (1S,2S)-MeTsDPEN, (1S,2S)-CsDPEN, (1S,2S)-MesitylDPEN, (1S,2S)-RsDPEN, (1S,2S)-TsDiOMeDPEN and the (1S,2S) form of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0.

E.61. The method according to embodiment E.60, where the chiral transition metal catalyst comprises as central metal Ru, Rh or Ir, and comprises a chiral ligand selected from the group consisting of (1S,2S)-TsDPEN, (1S,2S)—$CF_3$TsDPEN, (1S,2S)-MsDPEN, (1S,2S)-MeMsDPEN, (1S,2S)-MeTsDPEN, (1S,2S)-CsDPEN, (1S,2S)-MesitylDPEN, (1S,2S)-RsDPEN, (1S,2S)-TsDiOMeDPEN and the (1S,2S) form of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl; and m and n are 0.

E.62. The method according to any of embodiments E.51 to E.59, where the chiral transition metal catalyst comprises as central metal Ru, Rh or Ir, and comprises a chiral ligand selected from the group consisting of (1S,2S)-DPEN, (1S,2S)-TsDPEN, (1S,2S)—$CF_3$TsDPEN, (1S,2S)-MsDPEN, (1S,2S)-MeMsDPEN, (1S,2S)-MeTsDPEN, (1S,2S)-FsDPEN, (1S,2S)-TripsMesitylDPEN, (1S,2S)-CsDPEN, (1S,2S)-MesitylDPEN, (1S,2S)-RsDPEN and (1S,2S)-TsDiOMeDPEN; or is a catalyst containing Ru as central metal and at least one ligand selected from the (1S,2S) form of compounds of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0.

E.63. The method according to embodiment E.62, where the chiral transition metal catalyst comprises as central metal Ru, Rh or Ir, and comprises a chiral ligand selected from the group consisting of (1S,2S)-TsDPEN, (1S,2S)—$CF_3$TsDPEN, (1S,2S)-MsDPEN, (1S,2S)-MeMsDPEN, (1S,2S)-MeTsDPEN, (1S,2S)-CsDPEN, (1S,2S)-MesitylDPEN, (1S,2S)-RsDPEN and (1S,2S)-TsDiOMeDPEN; or is a catalyst of the following formula

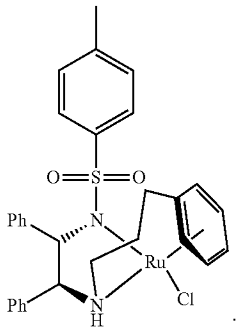

E.64. The method according to any of embodiments E.1 to E.50, for preparing 2-[(2R)-2-(2-chlorothiazol-5-yl)-2-hydroxy-ethyl]sulfanyl-6-hydroxy-3-methyl-5-phenyl-pyrimidin-4-one of the formula (I-R)

(I-R)

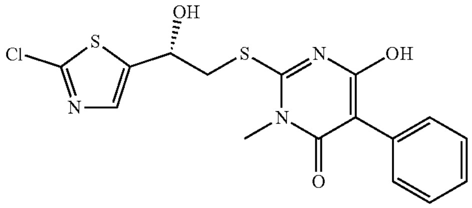

in an enantiomeric excess of at least 55% ee.

E.65. The method according to embodiment E.64, for preparing 2-[(2R)-2-(2-chlorothiazol-5-yl)-2-hydroxy-ethyl]sulfanyl-6-hydroxy-3-methyl-5-phenyl-pyrimidin-4-one of the formula (I-R) in an enantiomeric excess of at least 60% ee.

E.66. The method according to embodiment E.65, for preparing 2-[(2R)-2-(2-chlorothiazol-5-yl)-2-hydroxy-ethyl]sulfanyl-6-hydroxy-3-methyl-5-phenyl-pyrimidin-4-one of the formula (I-R) in an enantiomeric excess of at least 70% ee.

E.67. The method according to embodiment E.66, for preparing 2-[(2R)-2-(2-chlorothiazol-5-yl)-2-hydroxy-ethyl]sulfanyl-6-hydroxy-3-methyl-5-phenyl-pyrimidin-4-one of the formula (I-R) in an enantiomeric excess of at least 80% ee.

E.68. The method according to embodiment E.67, for preparing 2-[(2R)-2-(2-chlorothiazol-5-yl)-2-hydroxy-ethyl]sulfanyl-6-hydroxy-3-methyl-5-phenyl-pyrimidin-4-one of the formula (I-R) in an enantiomeric excess of at least 90% ee.

E.69. The method according to any of embodiments E.64 to E.68, where the chiral transition metal catalyst comprises a chiral ligand selected from the group consisting of (1R,2R)-DPEN, (1R,2R)-TsDPEN, (1R,2R)—$CF_3$TsDPEN, (1R,2R)-MsDPEN, (1R,2R)-MeMsDPEN, (1R,2R)-MeTsDPEN, (1R,2R)-FsDPEN, (1R,2R)-TripsMesitylDPEN, (1R,2R)-CsDPEN, (1R,2R)-MesitylDPEN, (1R,2R)-RsDPEN, (1R,2R)-TsDiOMeDPEN and the (1R,2R) form of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0.

E.70. The method according to embodiment E.69, where the chiral transition metal catalyst comprises a chiral ligand selected from the group consisting of (1R,2R)-TsDPEN, (1R,2R)-$CF_3$TsDPEN, (1R,2R)-MsDPEN, (1R,2R)-MeMsDPEN, (1R,2R)-MeTsDPEN, (1R,2R)-CsDPEN, (1R,2R)-MesitylDPEN, (1R,2R)-RsDPEN, (1R,2R)-TsDiOMeDPEN and the (1R,2R) form of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0.

E.71. The method according to embodiment E.70, where the chiral transition metal catalyst comprises a chiral ligand selected from the group consisting of (1R,2R)-TsDPEN, (1R,2R)-$CF_3$TsDPEN, (1R,2R)-MsDPEN, (1R,2R)-MeMsDPEN, (1R,2R)-MeTsDPEN, (1R,2R)-CsDPEN, (1R,2R)-MesitylDPEN, (1R,2R)-RsDPEN, (1R,2R)-TsDiOMeDPEN and the (1R,2R) form of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl; and m and n are 0.

E.72. The method according to any of embodiments E.64 to E.69, where the chiral transition metal catalyst comprises as central metal Ru, Rh or Ir, and comprises a chiral ligand selected from the group consisting of (1R,2R)-DPEN, (1R,2R)-TsDPEN, (1R,2R)-$CF_3$TsDPEN, (1R,2R)-MsDPEN, (1R,2R)-MeMsDPEN, (1R,2R)-MeTsDPEN, (1R,2R)-FsDPEN, (1R,2R)-TripsMesitylDPEN, (1R,2R)-CsDPEN, (1R,2R)-MesitylDPEN, (1R,2R)-RsDPEN, (1R,2R)-TsDiOMeDPEN and the (1R,2R) form of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0.

E.73. The method according to embodiment E.72, where the chiral transition metal catalyst comprises as central metal Ru, Rh or Ir, and comprises a chiral ligand selected from the group consisting of (1R,2R)-TsDPEN, (1R,2R)—$CF_3$TsDPEN, (1R,2R)-MsDPEN, (1R,2R)-MeMsDPEN, (1R,2R)-MeTsDPEN, (1R,2R)-CsDPEN, (1R,2R)-MesitylDPEN, (1R,2R)-RsDPEN, (1R,2R)-TsDiOMeDPEN and the (1R,2R) form of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0.

E.74. The method according to embodiment E.73, where the chiral transition metal catalyst comprises as central metal Ru, Rh or Ir, and comprises a chiral ligand selected from the group consisting of (1R,2R)-TsDPEN, (1R,2R)-$CF_3$TsDPEN, (1R,2R)-MsDPEN, (1R,2R)-MeMsDPEN, (1R,2R)-MeTsDPEN, (1R,2R)-CsDPEN, (1R,2R)-MesitylDPEN, (1R,2R)-RsDPEN, (1R,2R)-TsDiOMeDPEN and the (1R,2R) form of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl; and m and n are 0.

E.75. The method according to any of embodiments E.64 to E.72, where the chiral transition metal catalyst comprises as central metal Ru, Rh or Ir, and comprises a chiral ligand selected from the group consisting of (1R,2R)-DPEN, (1R,2R)-TsDPEN, (1R,2R)-$CF_3$TsDPEN, (1R,2R)-MsDPEN, (1R,2R)-MeMsDPEN, (1R,2R)-MeTsDPEN, (1R,2R)-FsDPEN, (1R,2R)-TripsMesitylDPEN, (1R,2R)-CsDPEN, (1R,2R)-MesitylDPEN, (1R,2R)-RsDPEN, (1R,2R)-TsDiOMeDPEN, or is a catalyst containing Ru as central metal and at least one ligand selected from the (1R,2R)

form of compounds of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0.

E.76. The method according to embodiment 75, where the chiral transition metal catalyst comprises as central metal Ru, Rh or Ir, and comprises a chiral ligand selected from the group consisting of (1R,2R)-TsDPEN, (1R,2R)-$CF_3$TsDPEN, (1R,2R)-MsDPEN, (1R,2R)-MeMsDPEN, (1R,2R)-MeTsDPEN, (1R,2R)-CsDPEN, (1R,2R)-MesitylDPEN, (1R,2R)-RsDPEN and (1R,2R)-TsDiOMeDPEN, or is a catalyst of the following formula:

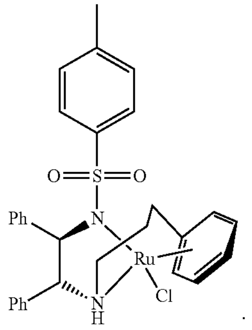

E.77. The method according to any of the preceding embodiments, where the reaction is carried out at a temperature of from −20 to 120° C.

E.78. The method according to embodiment E.77, where the reaction is carried out at a temperature of from −15 to 25° C.

E.79. The method according to embodiment E.77, where the reaction is carried out at a temperature of from 30 to 100° C.

E.80. The method according to embodiment E.79, where the reaction is carried out at a temperature of from 50 to 90° C.

E.81. The method according to any of the preceding embodiments, where the reaction is carried out in the presence of a solvent.

E.82. The method according to embodiment E.81, where the solvent is selected from the group consisting of polar protic solvents, polar aprotic solvents, $C_1$-$C_4$-alkyl acetates, chlorinated alkanes, aromatic solvents, heterocyclic solvents, mixtures of the aforementioned solvents and mixtures of the aforementioned solvents with water;

where in case that formic acid and/or a base which is liquid at the reaction temperature is used, the reaction can alternatively be carried out neat.

E.83. The method according to embodiment E.82, where the solvent is selected from the group consisting of $C_1$-$C_4$-alkanols, glycols, dimethylformamide, diethylformamide, dibutylformamide, dimethylacetamide, tetrahydrofuran, 2-methyltetrahydrofuran, the dioxanes, dimethylsulfoxide, acetonitrile, N-methylpyrrolidone, N-(n-butyl)-pyrrolidone, N-(tert-butyl)-pyrrolidone, sulfolane, dimethylcarbonate, diethylcarbonate, propylene carbonate, γ-valerolactone, N,N,N',N'-tetrabutyl urea, 1,3-dimethyl-2-imidazolinone, ethyl acetate, isopropyl acetate, dichloromethane, trichloromethane, dichloroethane, benzene, toluene, α,α,α-trifluorotoluene (benzotrifluoride), the xylenes, fluorobenzene, chlorobenzene, dichlorobenzene, anisole (methoxybenzene) 4-formyl-morpholine, dihydrolevoglucosenone (Cyrene®), mixtures of the aforementioned solvents and mixtures of the aforementioned solvents with up to 15% by weight, preferably up to 10% by weight, in particular up to 5% by weight, specifically up to 3% by weight of water, relative to the overall weight of the solvent.

E.84. The method according to embodiment E.83, where the solvent is selected from the group consisting of from dimethylformamide, dimethylacetamide, tetrahydrofuran, 2-methyltetrahydrofuran, dimethylsulfoxide, sulfolane, ethyl acetate, ethanol, dichloromethane, trichloromethane, dichloroethane, α,α,α-trifluorotoluene (benzotrifluoride), fluorobenzene, chlorobenzene, dichlorobenzene, anisole (methoxybenzene), and mixtures thereof.

E.85. The method according to embodiment E.84, where the solvent is selected from the group consisting of from dimethylformamide, dimethylacetamide and mixtures thereof.

E.86. The method according to any of the preceding embodiments, where during the reaction an inert gas different from $CO_2$ is sparged through the reaction mixture; or where alternatively or additionally the reaction is carried out under reduced pressure.

E.87. The method according to embodiment E.86, where gas different from $CO_2$ is selected from the group consisting of argon, nitrogen, and mixtures of oxygen and nitrogen containing 1-8 vol-% of oxygen, relative to the total amount of the oxygen/nitrogen mixture.

E.88. The method according to embodiment E.87, where gas different from $CO_2$ is nitrogen.

E.89. The method according to any of the preceding embodiments, where the reaction is carried out in the presence of an additive selected from the group consisting of diethyl phosphite, borate esters and zinc salts.

E.90. The method according to embodiment E.89, where the additive is selected from the group consisting of diethyl phosphite and zinc salts.

E.91. The method according to embodiment E.90, where the additive is diethyl phosphite.

E.92. The method according to any of embodiments E.889 to E.91, where the zinc salts are selected from the group consisting of zinc halides, zinc acetate and zinc trifluoromethane sulfonate.

E.93. The method according to embodiment E.92, where the additive is zinc acetate.

E.94. The method according to any of embodiments E.89 to E.93, where the additive is used in such an amount that the molar ratio of additive and the compound 1 is in the range of from 1:10000 to 10:1.

E.95. The method according to embodiment E.94, where the molar ratio of additive and the compound 1 is in the range of from 1:10000 to 5:1.

E.96. The method according to embodiment E.95, where the molar ratio of additive and the compound 1 is in the range of from 1:10000 to 2:1, e.g. from 1:10000 to 1:2 or 1:10000 to 1:10.

E.97. The method according to any of the preceding embodiments, where after completion of the reaction the pyrimidinone of the formula (I) in enantiomerically enriched form is isolated from the reaction mixture, where isolation comprises adding water to the reaction mixture, isolating and optionally purifying the pyrimidinone of the formula (I) precipitated upon addition of water; or where isolation comprises setting the pH of the reaction mixture acidic; removing at least a part of the solvent, if any, to obtain a concentrate; adding water and a solvent which has low or no miscibility with water to the concentrate; extracting the pyrimidinone of the formula (I) into the solvent which has low or no miscibility with water; and isolating the pyrimidinone of the formula (I) from the extract.

E.98. The method according to embodiment E.97, where the solvent which has low or no miscibility with water is selected from the group consisting of 2-methyltetrahydrofuran, methyl acetate, ethyl acetate, isopropyl acetate, n-butyl acetate, isobutyl acetate, methylisopropyl ketone, and chlorobenzene.

E.99. 2-[2-(2-Chlorothiazol-5-yl)-2-hydroxy-ethyl]sulfanyl-6-hydroxy-3-methyl-5-phenyl-pyrimidin-4-one of the formula (I) or an enatiomerically enriched form thereof (I)

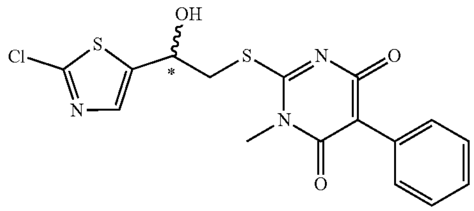

where the asterisk * shows the stereogenic center.

The reaction sequence of the method of the invention can be depicted as follows:

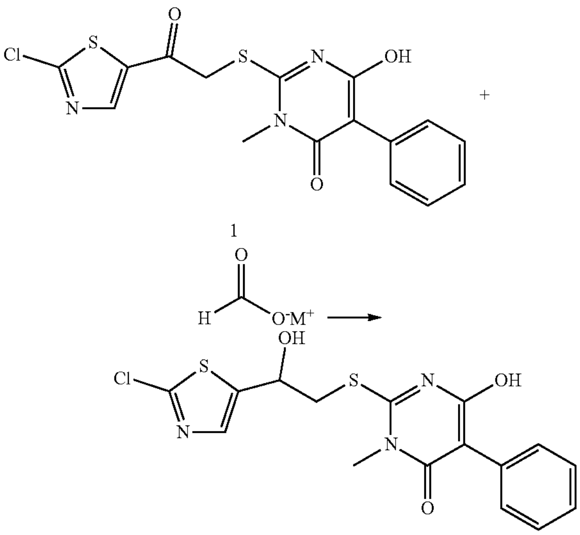

1

(I)

Here, only the formate is shown as reduction agent, but formic acid (in the presence of a base) or a mixture of formic acid and a formate (optionally in the presence of a base) can be used alternatively.

The reaction can be classified as an asymmetric transfer hydrogenation.

$M^+$ is preferably selected from the group consisting of alkali metal cations, ammonium cations of the formula $[NHR^1R^2R^3]^+$, where $R^1$, $R^2$ and $R^3$, independently of each other, are selected from the group consisting of hydrogen, $C_1$-$C_6$-alkyl, $C_3$-$C_6$-cycloalkyl, $C_1$-$C_4$-alkoxy and $C_1$-$C_4$-alkoxy-$C_1$-$C_4$-alkyl, protonated diamines of the formula $NR^1R^2$-A-$NR^3R^4$, where $R^1$, $R^2$, $R^3$ and $R^4$, independently of each other, are selected from the group consisting of hydrogen, $C_1$-$C_6$-alkyl, $C_3$-$C_6$-cycloalkyl, $C_1$-$C_4$-alkoxy and $C_1$-$C_4$-alkoxy-$C_1$-$C_4$-alkyl, and A is $(CH_2)_2$ or $(CH_2)_3$; and protonated 5- or 6-membered saturated heterocyclic rings containing one nitrogen atom as ring member and optionally one further heteroatom selected from N and O as ring member, where the ring may carry 1 to 6 $C_1$-$C_4$-alkyl groups and/or 1 or 2 OH groups.

In the ammonium cations of the formula $[NHR^1R^2R^3]^+$ derived from monoamines, preferably at most one of $R^1$, $R^2$ and $R^3$ is hydrogen and the other two or all three thereof, independently of each other, are selected from the group consisting of hydrogen, $C_1$-$C_6$-alkyl, $C_3$-$C_6$-cycloalkyl and $C_1$-$C_4$-alkoxy-$C_1$-$C_4$-alkyl. Such ammonium cations are the protonated form of the corresponding amines $NR^1R^2R^3$. In the diamines $NR^1R^2$-A-$NR^3R^4$, preferably at least one of $R^1$, $R^2$, $R^3$ and $R^4$ is not hydrogen. More preferably, none of $R^1$, $R^2$, $R^3$ and $R^4$ is hydrogen. Preferably, $R^1$, $R^2$, $R^3$ and $R^4$ are independently of each other $C_1$-$C_4$-alkyl.

Protonated diamines $NR^1R^2$-A-$NR^3R^4$ can be monoprotonated ($[NHR^1R^2$-A-$NR^3R^4]^+$) or bisprotonated ($[NHR^1R^2$-A-$NHR^3R^4]^{2+}$). In the latter case, $M^+$ is more precisely depicted as $(M^{2+})_{1/2}$ or $([NHR^1R^2$-A-$NHR^3R^4]^{2+})_{1/2}$.

The protonated 5- or 6-membered saturated heterocyclic rings are preferably derived from pyrrolidine, pyrazolidine, imidazolidine, oxazolidine, isoxazolidine, piperidine, piperazine, or morpholine. In case of two nitrogen ring atoms, like in pyrazolidine, imidazolidine or piperazine, the rings can also be bisprotonated. The protonated 5- or 6-membered saturated heterocyclic rings can carry 1 to 6 $C_1$-$C_4$-alkyl and/or 1 or 2 hydroxyl groups on the nitrogen and/or carbon ring atoms. Particularly, the protonated saturated heterocyclic rings are 6-membered and thus preferably derived from piperidine, piperazine, or morpholine, which may carry 1 to 6 $C_1$-$C_4$-alkyl and/or 1 or 2 hydroxyl groups on the nitrogen and/or carbon ring atoms.

In particular, $M^+$ is selected from the group consisting of $Li^+$, $Na^+$, $K^+$, $Cs^+$, $NH_4^+$, $[NH_2(C_2H_6)_2]^+$, $[NH(C_2H_6)_3]^+$, $[NH(CH_2CH_2CH_2CH_3)_3]^+$, $[NH(C_2H_6)(CH(CH_3)_2]^+$, $[NH(CH_3)_2(CH(CH_3)]^+$, $[NH_2(C_2H_6)(C(CH_3)_3]^+$, $[NH_2(CH(CH_3)_2)(C(CH_3)_3]^+$, $[NH_2(C_2H_4OCH_3)(CH_3)]^+$, $[NH(cyclohexyl)_2(CH_3)]^+$, $[NH(cyclohexyl)(CH_3)_2]^+$, protonated N,N,N',N'-tetramethylethylenediamine, protonated N,N,N',N'-tetramethylpropylene-1,3-diamine, protonated piperdine, protonated N-methylpiperidine, protonated 2,2,6,6-tetramethylpiperidine, protonated N-methyl-2,6,6-tetramethylpiperidine, protonated N-methyl-4-hydroxy-2,2,6,6-tetramethylpiperidine, protonated morpholine, and protonated N-methylmorpholine. More particularly, $M^+$ is selected from the group consisting of alkali metal cations (such as $Li^+$, $Na^+$, $K^+$ or $Cs^+$) and ammonium cations of the formula $[NHR^1R^2R^3]^+$, where $R^1$, $R^2$ and $R^3$, independently of each other, are selected from the group consisting of hydrogen and $C_1$-$C_6$-alkyl, where preferably at least one, preferably at least two of $R^1$, $R^2$ and $R^3$ are $C_1$-$C_6$-alkyl (such as $[NH_2(C_2H_6)_2]^+$, $[NH(C_2H_5)_3]^+$, $[NH(CH_2CH_2CH_2CH_3)_3]^+$, $[NH(C_2H_6)(CH(CH_3)_2]^+$, $[NH(CH_3)_2(CH(CH_3)]^+$, $[NH_2(C_2H_6)$ $(C(CH_3)_3]^+$, or $[NH_2(CH(CH_3)_2)(C(CH_3)_3]^+)$. Specifically, $M^+$ is selected from the group consisting of $Na^+$, $K^+$, $[NH(C_2H_6)_3]^+$, $[NH(CH_2CH_2CH_2CH_3)_3]^+$ and $[NH(C_2H_5)(CH(CH_3)_2]^+$, more specifically from $Na^+$, $K^+$, $[NH(C_2H_5)_3]^+$, $[NH(CH_2CH_2CH_2CH_3)_3]^+$ and $[NH(C_2H_5)(CH(CH_3)_2]^+$, and very specifically from $[N H(C_2H_5)_3]^+$, $[NH(CH_2CH_2CH_2CH_3)_3]^+$ and $[NH(C_2H_5)(CH(CH_3)_2]^+$.

The reduction agent is selected from the group consisting of formic acid HC(═O)OH, formates of the formula $HC({=}O)O^-M^+$ and mixtures of formic acid HC(═O)OH and one or more formates of the formula $HC({=}O)O^-M^+$, where $M^+$ is a cation equivalent. If formic acid is used as reduction agent, the reaction is mandatorily carried out in the presence of a base. Depending on the amount of base, formic acid can be converted partially or completely to the corresponding formate in situ.

The formates of the formula $HC({=}O)O^-M^+$ and mixtures of formic acid HC(═O)OH and one or more formates of the formula $HC({=}O)O^-M^+$ can be used in the reaction either in preformed form or can be formed in situ by mixing formic acid with the corresponding base in the adequate molar ratio. For obtaining formates or mixtures of formic acid and a formate wherein $M^+$ is a metal cation, e.g. an alkali metal cation, formic acid is for example mixed with a metal hydroxide, e.g. an alkali metal hydroxide, or with a metal carbonate, e.g. an alkali metal carbonate. For obtaining formates or mixtures of formic acid and a formate wherein $M^+$ is an ammonium cation or a protonated diamine or a protonated heterocyclic ring as described above, formic acid is suitably mixed with the corresponding monoamine $NR^1R^2R^3$, diamine $NR^1R^2$-A-$NR^3R^4$ or the 5- or 6-membered saturated heterocyclic ring defined above.

In context of the present invention, the base optionally or mandatorily used is one different from the formate(s) $HC({=}O)O^-M^+$.

The base which is optionally or mandatorily used, depending on the reduction agent, is preferably selected from the group consisting of alkali metal hydroxides, amines of the formula $NR^1R^2R^3$, where $R^1$, $R^2$ and $R^3$, independently of each other, are selected from the group consisting of hydrogen, $C_1$-$C_6$-alkyl, $C_3$-$C_6$-cycloalkyl, $C_1$-$C_4$-alkoxy and $C_1$-$C_4$-alkoxy-$C_1$-$C_4$-alkyl, where at least one of $R^1$, $R^2$ and $R^3$ is not hydrogen; diamines of the formula $NR^1R^2$-A-$NR^3R^4$, where $R^1$, $R^2$, $R^3$ and $R^4$, independently of each other, are selected from the group consisting of hydrogen, $C_1$-$C_6$-alkyl, $C_3$-$C_6$-cycloalkyl, $C_1$-$C_4$-alkoxy and $C_1$-$C_4$-alkoxy-$C_1$-$C_4$-alkyl, and A is $(CH_2)_2$ or $(CH_2)_3$; and a 5- or 6-membered saturated heterocyclic ring containing one nitrogen atom as ring member and optionally one further heteroatom selected from N and O as ring member, where the ring may carry 1 to 6 $C_1$-$C_4$-alkyl groups and/or 1 or 2 OH groups.

If a formate or a mixture of formic acid and formate is used as reduction agent, the base corresponds preferably to the cation $M^+$ in the formate; especially if $M^+$ is derived from a monoamine $NR^1R^2R^3$, a diamine $NR^1R^2$-A-$NR^3R^4$, or said 5- or 6-membered saturated heterocyclic ring.

More preferably, the base is selected from the group consisting of LiOH, NaOH, KOH, diethylamine, triethylamine, tributylamine, diisopropylethylamine, dimethylisopropylamine, ethyl-tert-butylamine, isopropyl-tert-butylamine, (2-methoxyethyl)methylamine, N,N-dicyclohexylmethylamine, N-cyclohexyldimethylamine, N,N,N',N'-tetramethylethylenediamine, N,N,N',N'-tetramethylpropylene-1,3-diamine, piperdine, N-methylpiperidine, 2,2,6,6-tetramethylpiperidine, N-methyl-2,6,6-tetramethylpiperidine, N-methyl-4-hydroxy-2,2,6,6-tetramethylpiperidine, morpholine and N-methylmorpholine, where the bases can be used in supported from (i.e. on a support material). Among these, preference is given to amines $NR^1R^2R^3$, where $R^1$, $R^2$ and $R^3$, independently of each other, are selected from the group consisting of hydrogen and $C_1$-$C_6$-alkyl, where at least one of $R^1$, $R^2$ and $R^3$ is $C_1$-$C_6$-alkyl, such as diethylamine, triethylamine, tributylamine, diisopropylethylamine, dimethylisopropylamine, ethyl-tert-butylamine, or isopropyl-tert-butylamine. Specifically, the base is selected from triethylamine, tributylamine and diisopropylethylamine. Preference is also given to NaOH and KOH.

Suitable support materials for bases/supported bases are for example silica ($SiO_2$) and organic polymers, such as polystyrene or acrylic ester based supports, for example polymers typically used in ion exchange resins, e.g. styrene (co)polymers containing sulfonic acid groups, specifically styrene-divinyl benzene copolymers containing sulfonic acid groups. Commercial examples for such ion exchanger supports are materials commercialized under the Lewatit® (Lanxess), Purolite® (The Purolite Company), Dowex® (Dow Chemical Company), Amberlite® (Rohm and Haas Company) or Amberlyst® (Rohm and Haas Company) brands.

If a formate $HC({=}O)O^-M^+$ is used as only reduction agent, it is expedient to use this in admixture with water.

If a mixture of formic acid HC(═O)OH and one or more formates of the formula $HC({=}O)O^-M^+$ is used as reduction agent, formic acid and the formate(s) can be used in any mixing ratio. If however formic acid predominates substantially in the mixture (i.e. is present in an amount of at least 90 mol %), it is expedient to carry out the reaction in the presence of a base. In inversely the formate(s) predominate(s) substantially in the mixture (i.e. is present in an amount of at least 90 mol %), it is expedient to carry out the reaction in the presence of water.

Preferably, formic acid is used as a reduction agent. It is thus mandatory to carry out the reaction in the presence of a base.

Formic acid and the base are preferably used in a molar ratio of from 100:1 to 1:10, preferably from 10:1 to 1:5, in particular from 5:1 to 1:5, and specifically from 5:1 to 1:1.

Compound 1 and the reduction agent are preferably used in a molar ratio of from 1:1 to 1:10, more preferably from 1:1 to 1:5.

The chiral transition metal catalyst is preferably selected from group VIII metal catalysts. Group VIII metal catalysts refer to catalysts having a metal from group VIII of the periodic system of elements as central metal. Group VIII relates to the IU PAC group definition valid before 1985 and corresponds to groups 8, 9 and 10 of the current IU-PAC group designation. Group 8 comprises Fe, Ru and Os, group 9 Co, Rh and Ir and group 10 Ni, Pd and Pt. Preference is given to group 8 and 9 metal catalysts. Among these, in turn, preference is given to Ru, Rh and Ir catalysts. Specifically, the chiral transition metal catalyst is one with Rh or Ir as central atom.

Preferably, the chiral transition metal catalyst, calculated on the basis of the transition metal content, is used in an amount of 0.01 to 10 mol %, more preferably from 0.05 to 5 mol-%, even more preferably from 0.1 to 5 mol-%,and specifically from 0.1 to 2 mol-%, relative to 1 mol of the compound 1.

Chirality of the chiral transition metal catalyst is preferably based on the presence of one or more chiral ligands coordinatively bound to the central transition metal.

The chiral transition metal catalyst can be used in preformed form. In the preformed catalyst, the central metal is coordinatively bound to one or more chiral ligands. Alternatively, the chiral transition metal catalyst is formed in situ by reaction of a transition metal precursor compound and one or more chiral ligands.

The chiral ligands are preferably selected from bidentate amine-based chiral ligands. Suitable bidentate amine-based chiral ligands are based on 1,2-ethylenediamine substituted thusly that at least one of the carbon atoms carrying the amino groups is asymmetric; i.e. is a stereogenic center. Preferably, one or both of the carbon atoms of the 1,2-ethylenediamine ligand carry a phenyl, naphthyl or cyclohexyl ring or the two carbon atoms are part of a ring system imparting chirality. More preferably, the chiral ligands are selected from the group consisting of chiral 1,2-diphenyl-ethylene-1,2-diamines, 1,2-cyclohexanediamines, and 1,2-bis(methylamino)cyclohexanes.

Even more preferably, the chiral ligands are selected from the group consisting of chiral 1,2-diphenyl-ethylene-1,2-diamines, and in particular from the chiral forms of 1,2-diphenyl-ethylene-1,2-diamines of the formula (II)

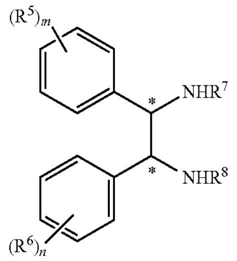

(II)

where the asterisk shows the stereogenic centers;

$R^5$ and $R^6$, independently of each other, are selected from the group consisting of OH, halogen, $C_1$-$C_4$-alkyl and $C_1$-$C_4$-alkoxy;

$R^7$ and $R^8$, independently of each other, are selected from the group consisting of hydrogen, $C_1$-$C_4$-alkyl, -L-phenyl, where the phenyl ring may carry 1, 2, 3, 4 or 5 substituents selected from the group consisting of $C_1$-$C_4$-alkyl, $C_1$-$C_4$-haloalkyl and $C_1$-$C_4$-alkoxy; and $SO_2R^9$;

L is a linker selected from the group consisting of $C_2$-$C_6$-alkylene, $C_1$-$C_3$-alkylene-O—$(CH_2)_p$, where p is 0, 1 or 2; and $C_1$-$C_3$-alkylene-(1,2-phenylene)-$(CH_2)_r$, where r is 0, 1 or 2;

$R^9$ is selected from the group consisting of $C_1$-$C_4$-alkyl, $C_1$-$C_4$-haloalkyl, phenyl, phenyl-$C_1$-$C_3$-alkyl, where phenyl in the two aforementioned radicals may carry 1, 2, 3, 4 or 5 substituents selected from the group consisting of halogen, $C_1$-$C_4$-alkyl, $C_1$-$C_4$-haloalkyl and $C_1$-$C_4$-alkoxy; naphthyl, $C_6$-$C_{10}$-bicycloalkyl-$C_1$-$C_3$-alkyl, where the bicycloalkyl ring may be substituted by 1, 2, 3, 4 or 5 substituents selected from the group consisting of $C_1$-$C_4$-alkyl and oxo; and $NR^{10}R^{11}$;

$R^{10}$ is hydrogen or $C_1$-$C_4$-alkyl;

$R^{11}$ is phenyl-$C_1$-$C_3$-alkyl, where the phenyl ring may carry 1, 2, 3, 4 or 5 substituents selected from the group consisting of halogen, $C_1$-$C_4$-alkyl, $C_1$-$C_4$-haloalkyl and $C_1$-$C_4$-alkoxy; and m and n, independently of each other, are 0, 1, 2, 3, 4 or 5.

Preferably, in compounds (II)

$R^5$ and $R^6$ are $C_1$-$C_4$-alkoxy;

one of $R^7$ and $R^8$ is selected from the group consisting of hydrogen, $C_1$-$C_4$-alkyl and -L-phenyl, where phenyl may carry 1, 2, 3, 4 or 5 substituents selected from the group consisting of $C_1$-$C_4$-alkyl, $C_1$-$C_4$-haloalkyl and $C_1$-$C_4$-alkoxy; and the other of $R^7$ and $R^8$ is selected from the group consisting of hydrogen and $SO_2R^9$;

L is a linker selected from the group consisting of linear $C_3$-$C_6$-alkylene, $(CH_2)_o$—O—$(CH_2)_p$, where p and o are independently 1 or 2; and $(CH_2)_q$-(1,2-phenylene)-$(CH_2)_r$, where q and r are independently 0, 1 or 2, where at least one of q and r is not 0;

$R^9$ is selected from the group consisting of $C_1$-$C_4$-alkyl, $C_1$-$C_4$-haloalkyl, phenyl which may carry 1, 2, 3, 4 or 5 substituents selected from the group consisting of halogen, $C_1$-$C_4$-alkyl, $C_1$-$C_4$-haloalkyl and $C_1$-$C_4$-alkoxy; $C_7$-bicycloalkyl-methyl, where the bicycloalkyl ring may be substituted by 1, 2 or 3 substituents selected from the group consisting of $C_1$-$C_4$-alkyl and oxo; and $NR^{10}R^{11}$;

$R^{10}$ is hydrogen or $C_1$-$C_4$-alkyl;

$R^{11}$ is phenyl-$(CH_2)_s$-alkyl, where s is 2 or 3 and where the phenyl ring may carry 1, 2, 3, 4 or 5 substituents selected from the group consisting of halogen, $C_1$-$C_4$-alkyl, $C_1$-$C_4$-haloalkyl and $C_1$-$C_4$-alkoxy; and m and n are both 0 or are both 1, and are preferably both 0.

To be chiral, either both stereogenic centers (i.e. the carbon atoms marked in formula II with an asterisk) have to be in the R configuration or both have to be in the S configuration. If one is S and the other is R, an achiral meso system results.

Such ligands are known from Noyori-type asymmetric transfer hydrogenations and are generally commercially available. Preferred ligands of the formula (II) are the chiral forms (i.e. the (1S,2S) or (1R,2R) forms; positions 1 and 2 relate to the two carbon atoms marked in formula II with the asterisk which carry the phenyl rings and the amino groups) of DPEN, TsDPEN, $CF_3$TsDPEN, MsDPEN, MeMsDPEN, MeTsDPEN, FsDPEN, TripsMesitylDPEN, CsDPEN, MesitylDPEN, RsDPEN, TsDiOMeDPEN and of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0. The acronyms correspond to following formulae:

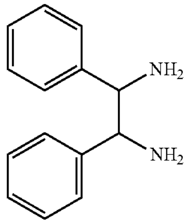

DPEN

-continued
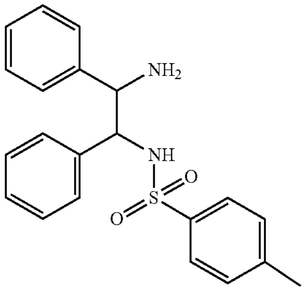
TsDPEN
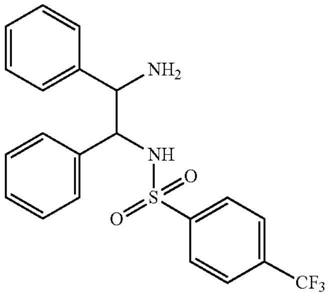
$CF_3$ TsDPEN
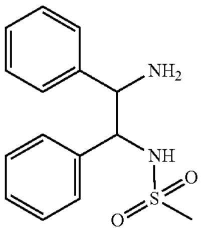
MsDPEN
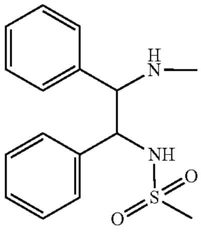
MeMsDPEN
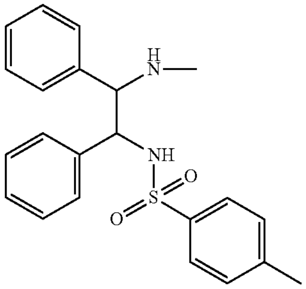
MeTsDPEN
-continued
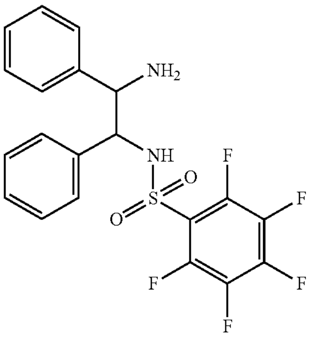
FsDPEN
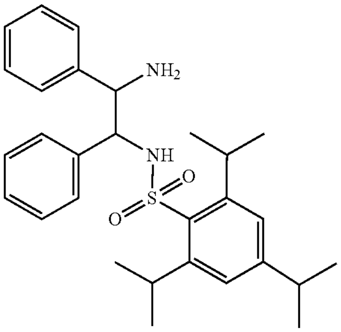
TripsMesitylDPEN
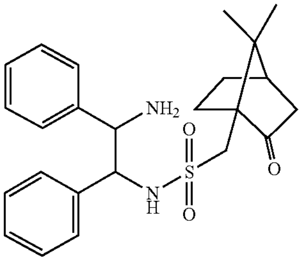
CsDPEN
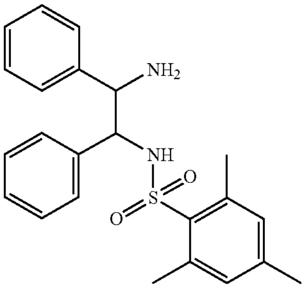
MesitylDPEN -continued

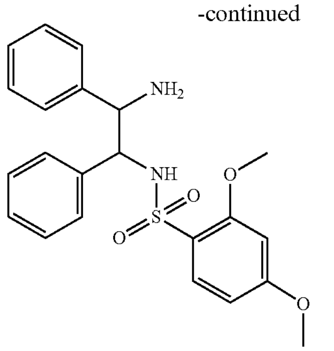

RsDPEN

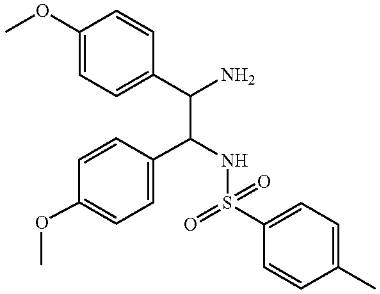

TsDiOMeDPEN

In addition to the two carbon atoms marked in formula II with the asterisk which carry the phenyl rings and the amino groups, CsDPEN has two further stereogenic centers in the camphor moiety (to be more precise on the norbornanone ring), namely at the carbon atoms which form the bridge points (positions 1 and 4; position 1 being the carbon ring atom bound to —$CH_2$—$SO_2$—NH— . . . ). The stereochemistry of the camphor moiety does however not have a significant influence on the stereoselectivity of the hydrogenation reaction, so that CsDPEN derived from racemic camphor or from any of the camphor enantiomers (1S,4R or 1R,4S) or non-racemic mixtures of enantiomers can be used. In a specific embodiment, however, CsDPEN is derived from the 1S,4R enantiomer, i.e. specifically, N-[(1S,2S)-2-amino-1,2-diphenyl-ethyl]-1-[(1S,4R)-7,7-dimethyl-2-oxo-norbornan-1-yl]methanesulfonamide as (1S,2S)-CsDPEN and N-[(1R,2R)-2-amino-1,2-diphenyl-ethyl]-1-[(1S,4R)-7,7-dimethyl-2-oxo-norbornan-1-yl]methanesulfonamide as (1R,2R)-CsDPEN.

The chiral transition metal catalyst is in particular selected from catalysts containing Ru, Rh or Ir as central metal and at least one ligand selected from the group consisting of the (1R,2R) or (1S,2S) forms of DPEN, TsDPEN, $CF_3$TsDPEN, MsDPEN, MeMsDPEN, MeTsDPEN, FsDPEN, TripsMesitylDPEN, CsDPEN, MesitylDPEN, RsDPEN, TsDiOMeDPEN and of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0.

The chiral transition metal catalyst is more particularly selected from catalysts containing Ru, Rh or Ir as central metal and at least one ligand selected from the group consisting of the (1R,2R) or (1S,2S) forms of TsDPEN, $CF_3$TsDPEN, MsDPEN, MeMsDPEN, MeTsDPEN, CsDPEN, MesitylDPEN, RsDPEN, TsDiOMeDPEN and of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0. The chiral transition metal catalyst is even more particularly selected from catalysts containing Ru, Rh or Ir as central metal and at least one ligand selected from the group consisting of the (1R,2R) or (1S,2S) forms of TsDPEN, $CF_3$TsDPEN, MsDPEN, MeMsDPEN, MeTsDPEN, CsDPEN, MesitylDPEN, RsDPEN, TsDiOMeDPEN and of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl; and m and n are 0.

Specifically, the chiral transition metal catalyst is selected from catalysts containing Ru, Rh or Ir as central metal and at least one ligand selected from the group consisting of the (1R,2R) or (1S,2S) forms of DPEN, TsDPEN, $CF_3$TsDPEN, MsDPEN, MeMsDPEN, MeTsDPEN, FsDPEN TripsMesitylDPEN, CsDPEN, MesitylDPEN, RsDPEN and TsDiOMeDPEN; and a catalyst containing Ru as central metal and at least one ligand selected from the (1R,2R) or (1S,2S) form of compounds of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0. More specifically, the chiral transition metal catalyst is selected from catalysts containing Ru, Rh or Ir as central metal and at least one ligand selected from the group consisting of the (1R,2R) or (1S,2S) forms of TsDPEN, $CF_3$TsDPEN, MsDPEN, MeMsDPEN, MeTsDPEN, CsDPEN, MesitylDPEN, RsDPEN and TsDiOMeDPEN; and a catalyst containing Ru as central metal and at least one ligand selected from the (1R,2R) or (1S,2S) form of compounds of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0.

Very specifically, the chiral transition metal catalyst is selected from catalysts containing Ru, Rh or Ir as central metal and at least one ligand selected from the group consisting of the (1R,2R) or (1S,2S) forms of TsDPEN, $CF_3$TsDPEN, MsDPEN, MeMsDPEN, MeTsDPEN, CsDPEN, MesitylDPEN, RsDPEN and TsDiOMeDPEN; and a catalyst of the following formula

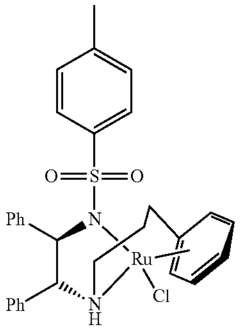

or

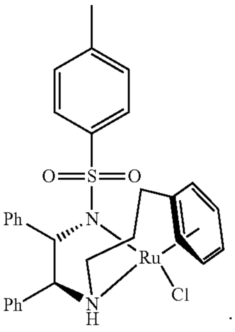

.

The chiral transition metal catalyst generally contains just one of the aforementioned bidentate amine ligands.

The optionally substituted phenyl ring in -L-phenyl as a meaning of $R^7$ or $R^8$, the optionally substituted phenyl ring in phenyl-$C_1$-$C_3$-alkyl is as a meaning of $R^9$ and the optionally substituted phenyl ring in phenyl-$C_1$-$C_3$-alkyl as a meaning of $R^{11}$ generally acts as an additional (tethered) ligand for the central metal. Such complexes containing aromatic ligands tethered to an ethylene diamine ligand are generally known as Wills catalysts.

In case that none of $R^7$ and $R^8$ is -L-phenyl or $SO_2R^9$ with $R^9$ being phenyl-$C_1$-$C_3$-alkyl or $NR^{10}R^{11}$, the catalyst preferably contains additionally a ligand selected from aromatic rings. Such ligands have generally a higher hapticity, i.e. they coordinate to the metal center via more than one atom, and specifically via an uninterrupted and contiguous series of atoms. Generally, they act as $\eta^5$ or $\eta^6$ ligands. Typical aromatic $\eta^5$ and $\eta^6$ ligands are substituted or unsubstituted benzene and substituted or unsubstituted cyclopentadiene. The aromatic rings are preferably selected from Cp, Cp*, benzene, p-cymene, mesitylene and hexamethylbenzene, in particular from Cp*, benzene, p-cymene, mesitylene and hexamethylbenzene, specifically from Cp*, p-cymene and mesitylene, and more specifically from Cp*. In tendency, 5-membered aromatic ligands, such as Cp and Cp* are better suited for Rh or Ir as central metal; and 6-membered aromatic ligands, such as benzene, p-cymene, mesitylene and hexamethylbenzene, are better suited for Ru as central metal. Thus, very specifically, the aromatic ring is Cp* if the central metal is Rh or Ir, and is p-cymene or mesitylene if the central metal is Ru.

Generally, the catalysts contain one or two further ligand of which at least one is replaced during reaction by a hydride ligand from the reduction agent under basic conditions. Generally, the further ligand is a halogen (e.g. Cl, Br or I; among which Cl is preferred) or sulfonate (e.g. triflate, mesylate, tosylate or nonaflate; among which triflate is preferred) ligand, in particular a halogen ligand, specifically Cl.

Catalyst precursors are generally salts of the central metal or complexes of the central metal with ligands different from the chiral ligand. In case of the preferably used catalysts with Ru, Rh or Ir as central metal, the catalyst precursor is specifically a binuclear complex containing an aromatic ring ligand and 2 halogen ligands. Non-exhaustive examples are $[Ru(para\text{-}cymene)Cl_2]_2$, $[Ru(mesitylene)Cl_2]_2$, $[Rh(III)Cl_2Cp^*]_2$, or $[Ir(III)Cl_2Cp^*]_2$. Such complexes are generally commercially available or can be prepared by standard methods.

Preformed catalysts are generally prepared by mixing the catalyst precursor with the chiral ligand. The reaction is generally carried out in a solvent. Depending on the catalyst precursor, it might be useful to carry out the reaction in the presence of a base. For instance, if the above-mentioned binuclear complexes of Ru, Rh or Ir containing an aromatic ring ligand and 2 halogen ligands are used as precursor compounds, the presence of a base is useful to ease or allow the reaction, i.e. the conversion of the binuclear complex into a mononuclear complex containing the desired chiral ligand. The catalyst precursor and the chiral ligand are generally mixed in a molar ratio of from 2:1 to 1:5, preferably 1.5:1 to 1:4 and in particular 1.2:1 to 1:3, where the molar ratio is based on the amount of transition metal (in mol) in the catalyst precursor. The formed catalyst can either be isolated before being used in the reaction or the obtained reaction mixture can be used without isolation of the complex.

If the catalyst is formed in situ, catalyst precursor and chiral ligand come into contact with each other in the presence of at least one of the reactants, e.g. of starting compound 1, the reduction agent and/or base (if used). Depending on the nature of the catalyst precursor, the formation of the catalyst might only start when a base is present. The base can be either the base mentioned above which is mandatorily used if HCOOH is used as reduction agent, or can be the formate if the reduction agent is used in this form. Preferably, catalyst precursor and chiral ligand are brought into contact with each other under conditions under which the catalyst precursor and chiral ligand can form the catalyst complex (in which the central metal is bound to the chiral ligand) before being contacted with starting compound 1. Thus, preferably, catalyst precursor and chiral ligand are brought into contact in the presence of the base (if used) and optionally also of the reduction agent, or in the presence of the formate if no additional base is used; and optionally also in the presence of a solvent, if the reaction is not to be carried out neat; and only thereafter the resulting mixture is brought into contact with starting compound 1. The catalyst precursor and the chiral ligand are generally used in a molar ratio of from 2:1 to 1:5, preferably from 1.5:1 to 1:4 and in particular from 1.2:1 to 1:3, where the molar ratio is based on the amount of transition metal (in mol) in the catalyst precursor.

In a preferred embodiment, the method of the invention serves for preparing 2-[(2S)-2-(2-chlorothiazol-5-yl)-2-hydroxy-ethyl]sulfanyl-6-hydroxy-3-methyl-5-phenyl-pyrimidin-4-one of the formula (I-S)

(I-S)

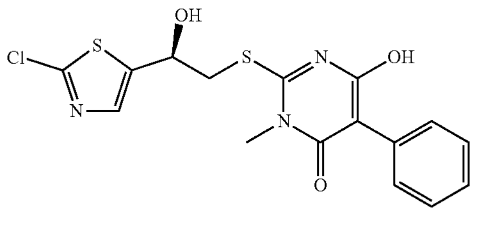

in enantiomeric excess, to be more precise in an enantiomeric excess of at least 55% ee, preferably at least 60% ee, more preferably at least 70% ee, in particular at least 80% ee and specifically at least 90% ee.

This is obtained by using the suitable chiral catalyst. This is preferably a transition metal catalyst, preferably a group VIII transition metal catalyst, more preferably a group 8 or 9 metal catalyst, in particular a Ru, Rh or Ir catalyst comprising a chiral ligand selected from the group consisting of (1S,2S)-DPEN, (1S,2S)-TsDPEN, (1S,2S)-

$CF_3$TsDPEN, (1S,2S)-MsDPEN, (1S,2S)-MeMsDPEN, (1S,2S)-MeTsDPEN, (1S,2S)-FsDPEN, (1S,2S)-TripsMesitylDPEN, (1S,2S)-CsDPEN, (1S,2S)-MesitylDPEN, (1S,2S)-RsDPEN, (1S,2S)-TsDiOMeDPEN and the (1S,2S) form of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0; preferably comprising a chiral ligand selected from the group consisting of (1S,2S)-TsDPEN, (1S,2S)-$CF_3$TsDPEN, (1S,2S)-MsDPEN, (1S,2S)-MeMsDPEN, (1S,2S)-MeTsDPEN, (1S,2S)-CsDPEN, (1S,2S)-MesitylDPEN, (1S,2S)-RsDPEN, (1S,2S)-TsDiOMeDPEN and the (1S,2S) form of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0; and more preferably comprising a chiral ligand selected from the group consisting of (1S,2S)-TsDPEN, (1S,2S)-$CF_3$TsDPEN, (1S,2S)-MsDPEN, (1S,2S)-MeMsDPEN, (1S,2S)-MeTsDPEN, (1S,2S)-CsDPEN, (1S,2S)-MesitylDPEN, (1S,2S)-RsDPEN, (1S,2S)-TsDiOMeDPEN and the (1S,2S) form of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl; and m and n are 0.

In particular, the chiral transition metal catalyst used for obtaining (I-S) in enantiomeric excess comprises as central metal Ru, Rh or Ir and comprises a chiral ligand selected from the group consisting of (1S,2S)-DPEN, (1S,2S)-TsDPEN, (1S,2S)-$CF_3$TsDPEN, (1S,2S)-MsDPEN, (1S,2S)-MeMsDPEN, (1S,2S)-MeTsDPEN, (1S,2S)-FsDPEN, (1S,2S)-TripsMesitylDPEN, (1S,2S)-CsDPEN, (1S,2S)-MesitylDPEN, (1S,2S)-RsDPEN and (1S,2S)-TsDiOMeDPEN; or is a catalyst containing Ru as central metal and at least one ligand selected from the (1S,2S) form of compounds of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0. More particularly, the chiral transition metal catalyst used for obtaining (I-S) in enantiomeric excess comprises as central metal Ru, Rh or Ir and comprises a chiral ligand selected from the group consisting of (1S,2S)-TsDPEN, (1S,2S)-$CF_3$TsDPEN, (1S,2S)-MsDPEN, (1S,2S)-MeMsDPEN, (1S,2S)-MeTsDPEN, (1S,2S)-CsDPEN, (1S,2S)-MesitylDPEN, (1S,2S)-RsDPEN and (1S,2S)-TsDiOMeDPEN; or is a catalyst containing Ru as central metal and at least one ligand selected from the (1S,2S) form of compounds of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0.

More specifically, the chiral transition metal catalyst selected from catalysts containing Ru, Rh or Ir as central metal and at least one ligand selected from the group consisting of (1S,2S)-TsDPEN, (1S,2S)-$CF_3$TsDPEN, (1S,2S)-MsDPEN, (1S,2S)-M eMsDPEN, (1S,2S)-MeTsDPEN, (1S,2S)-CsD PEN, (1S,2S)-MesitylDPEN, (1S,2S)-RsDPEN and (1S,2S)-TsDiOMeDPEN, or is catalyst of the following formula:

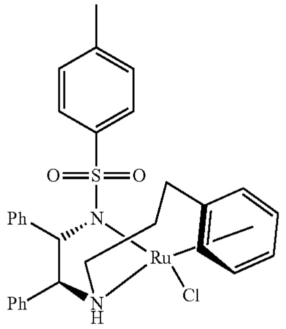
.

More particularly, the chiral transition metal catalyst used for obtaining (I-S) in enantiomeric excess comprises as central metal Ru, Rh or Ir and comprises a chiral ligand selected from the group consisting of (1S,2S)-DPEN, (1S,2S)-TsDPEN, (1S,2S)-$CF_3$TsDPEN, (1S,2S)-MsDPEN, (1S,2S)-MeMsDPEN, (1S,2S)-MeTsDPEN, (1S,2S)-FsDPEN, (1S,2S)-TripsMesitylDPEN, (1S,2S)-CsDPEN, (1S,2S)-MesitylDPEN, (1S,2S)-RsDPEN and (1S,2S)-TsDiOMeDPEN, and comprises additionally a ligand selected from aromatic rings such as substituted or unsubstituted benzene and substituted or unsubstituted cyclopentadiene, e.g. Cp, Cp*, benzene, p-cymene, mesitylene or hexamethylbenzene. As already explained above, 5-membered $\eta^5$ aromatic ligands, such as Cp and Cp* are better suited for Rh or Ir as central metal; therefore in the case of Rh and Ir as central metal, the additional aromatic ligand is preferably selected from Cp and Cp*, and is specifically Cp*. In case of Ru as central metal, the additional aromatic ligand is preferably selected from cymene and mesitylene. Even more particularly, the chiral transition metal catalyst used for obtaining (I-S) in enantiomeric excess comprises as central metal Ru, Rh or Ir and comprises a chiral ligand selected from the group consisting of (1S,2S)-TsDPEN, (1S,2S)-$CF_3$TsDPEN, (1S,2S)-MsDPEN, (1S,2S)-MeMsDPEN, (1S,2S)-MeTsDPEN, (1S,2S)-CsDPEN, (1S,2S)-MesitylDPEN, (1S,2S)-RsDPEN and (1S,2S)-TsDiOMeDPEN, and comprises additionally a ligand selected from aromatic rings such as substituted or unsubstituted benzene and substituted or unsubstituted cyclopentadiene, e.g. Cp, Cp*, benzene, p-cymene, mesitylene or hexamethylbenzene; in case of Rh and Ir as central metal specifically the $\eta^5$ ligand Cp*; and in case of Ru as central metal specifically cymene or mesitylene.

Moreover, the catalyst comprises a further ligand, in general a halide, specifically Cl, which is to be replaced by a hydride from the reduction agent.

Alternatively, the catalyst contains Ru as central metal and at least one ligand selected from the (1S,2S) form of compounds of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$- alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0. Generally, also this type of catalyst contains a further ligand, in general a halide or sulfonate, preferably halide, specifically Cl, which is to be replaced by a hydride from the reduction agent. This type of catalyst is specifically a compound of the following formula:

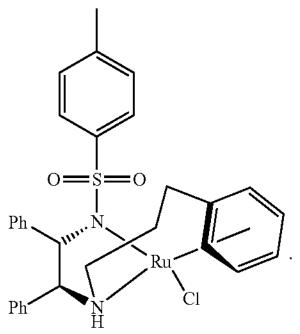

In another preferred embodiment, the method of the invention serves for preparing 2-[(2R)-2-(2-chlorothiazol-5-yl)-2-hydroxy-ethyl]sulfanyl-6-hydroxy-3-methyl-5-phenyl-pyrimidin-4-one of the formula (I-R)

(I-R)

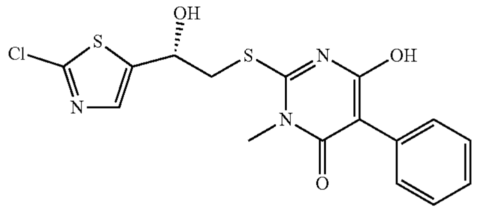

in enantiomeric excess, to be more precise in an enantiomeric excess of at least 55% ee, preferably at least 60% ee, more preferably at least 70% ee, in particular at least 80% ee and specifically at least 90% ee.

This is obtained by using the suitable chiral catalyst. This is preferably a transition metal catalyst, preferably a group VIII transition metal catalyst, more preferably a group 8 or 9 metal catalyst, in particular a Ru, Rh or Ir catalyst comprising a chiral ligand selected from the group consisting of (1R,2R)-DPEN, (1R,2R)-TsDPEN, (1R,2R)-$CF_3$TsDPEN, (1R,2R)-MsDPEN, (1R,2R)-MeMsDPEN, (1R,2R)-MeTsDPEN, (1R,2R)-FsDPEN, (1R,2R)-TripsMesitylDPEN, (1R,2R)-CsDPEN, (1R,2R)-MesitylDPEN, (1R,2R)-RsDPEN, (1R,2R)-TsDiOMeDPEN and of the (1R,2R) form of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0; preferably comprising a chiral ligand selected from the group consisting of (1R,2R)-TsDPEN, (1R,2R)-$CF_3$TsDPEN, (1R,2R)-MsDPEN, (1R,2R)-MeMsDPEN, (1R,2R)-MeTsDPEN, (1R,2R)-CsDPEN, (1R,2R)-MesitylDPEN, (1R,2R)-RsDPEN, (1R,2R)-TsDiOMeDPEN and of the (1R,2R) form of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0; and more preferably comprising a chiral ligand selected from the group consisting of (1R,2R)-TsDPEN, (1R,2R)-$CF_3$TsDPEN, (1R,2R)-MsDPEN, (1R,2R)-MeMsDPEN, (1R,2R)-MeTsDPEN, (1R,2R)-CsDPEN, (1R,2R)-MesitylDPEN, (1R,2R)-RsDPEN, (1R,2R)-TsDiOMeDPEN and of the (1R,2R) form of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl; and m and n are 0.

In particular, the chiral transition metal catalyst used for obtaining (I-R) in enantiomeric excess comprises as central metal Ru, Rh or Ir and comprises a chiral ligand selected from the group consisting of (1R,2R)-DPEN, (1R,2R)-TsDPEN, (1R,2R)-$CF_3$TsDPEN, (1R,2R)-MsDPEN, (1R,2R)-MeMsDPEN, (1R,2R)-MeTsDPEN, (1R,2R)-FsDPEN, (1R,2R)-TripsMesitylDPEN, (1R,2R)-CsDPEN, (1R,2R)-MesitylDPEN, (1R,2R)-RsDPEN and (1R,2R)-TsDiOMeDPEN; or is a catalyst containing Ru as central metal and at least one ligand selected from the (1R,2R) form of compounds of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0. More particularly, the chiral transition metal catalyst used for obtaining (I-R) in enantiomeric excess comprises as central metal Ru, Rh or Ir and comprises a chiral ligand selected from the group consisting of (1R,2R)-TsDPEN, (1R,2R)—$CF_3$TsDPEN, (1R,2R)-MsDPEN, (1R,2R)-MeMsDPEN, (1R,2R)-MeTsDPEN, (1R,2R)-CsDPEN, (1R,2R)-MesitylDPEN, (1R,2R)-RsDPEN and (1R,2R)-TsDiOMeDPEN; or is a catalyst containing Ru as central metal and at least one ligand selected from the (1R,2R) form of compounds of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0.

More specifically, the chiral transition metal catalyst selected from catalysts containing Ru, Rh or Ir as central metal and at least one ligand selected from the group consisting of (1R,2R)-TsDPEN, (1R,2R)-$CF_3$TsDPEN, (1R,2R)-MsDPEN, (1R,2R)-MeMsDPEN, (1R,2R)-MeTsDPEN, (1R,2R)-CsDPEN, (1R,2R)-MesitylDPEN, (1R,2R)-RsDPEN and (1R,2R)-TsDiOMeDPEN, or is a catalyst of the following formula:

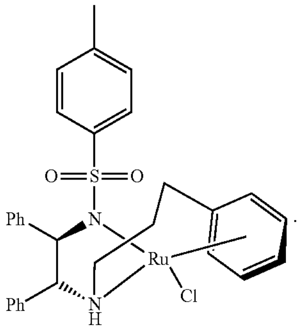

More particularly, the chiral transition metal catalyst used for obtaining (I-R) in enantiomeric excess comprises as central metal Ru, Rh or Ir and comprises a chiral ligand selected from the group consisting of (1R,2R)-DPEN, (1R,2R)-TsDPEN, (1R,2R)-$CF_3$TsDPEN, (1R,2R)-MsDPEN, (1R,2R)-MeMsDPEN, (1R,2R)-MeTsDPEN, (1R,2R)-FsDPEN, (1R,2R)-TripsMesitylDPEN, (1R,2R)-CsDPEN, (1R,2R)-MesitylDPEN, (1R,2R)-RsDPEN and (1R,2R)-Ts-DiOMeDPEN, and comprises additionally a ligand selected from aromatic rings such as substituted or unsubstituted benzene and substituted or unsubstituted cyclopentadiene, e.g. Cp, Cp*, benzene, p-cymene, mesitylene or hexamethylbenzene. As already explained above, 5-membered $\eta^5$ aromatic ligands, such as Cp and Cp* are better suited for Rh or Ir as central metal; therefore in the case of Rh or Ir as central metal, the additional aromatic ligand is preferably selected from Cp and Cp*, and is specifically Cp*. In case of Ru as central metal, the additional aromatic ligand is preferably selected from cymene and mesitylene. Even more particularly, the chiral transition metal catalyst used for obtaining (I-S) in enantiomeric excess comprises as central metal Ru, Rh or Ir and comprises a chiral ligand selected from the group consisting of (1R,2R)-TsDPEN, (1R,2R)—$CF_3$TsDPEN, (1R,2R)-MsDPEN, (1R,2R)-MeMsDPEN, (1R,2R)-MeTsDPEN, (1R,2R)-CsD PEN, (1R,2R)-MesitylDPEN, (1R,2R)-RsDPEN and (1R,2R)-TsDiOMeDPEN, and comprises additionally a ligand selected from aromatic rings such as substituted or unsubstituted benzene and substituted or unsubstituted cyclopentadiene, e.g. Cp, Cp*, benzene, p-cymene, mesitylene or hexamethylbenzene; in case of Rh or Ir as central metal specifically the $\eta^5$ ligand Cp*; and in case of Ru as central metal specifically cymene or mesitylene.

Moreover, the catalyst comprises a further ligand, in general a halide, specifically Cl, which is to be replaced by a hydride from the reduction agent.

Alternatively, the catalyst contains Ru as central metal and at least one ligand selected from the (1R,2R) form of compounds of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0. Generally, also this type of catalyst contains a further ligand, in general a halide or sulfonate, preferably halide, specifically Cl, which is to be replaced by a hydride from the reduction agent. This type of catalyst is specifically a compound of the following formula:

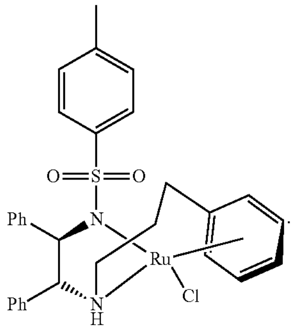

The reaction can be carried out in the presence of a solvent. The solvent is preferably selected from the group consisting of polar protic solvents, polar aprotic solvents, chlorinated alkanes, aromatic solvents, heterocyclic solvents, mixtures of the aforementioned solvents and mixtures of the aforementioned solvents with water.

Polar protic solvents are solvents without a functional group from which a proton can dissociate. Examples of suitable polar protic solvents are $C_1$-$C_4$-alkanols, fluorinated $C_1$-$C_4$-alkanols, glycols, mixtures thereof and mixtures thereof with water. $C_1$-$C_4$-Alkanols are for example methanol, ethanol, n-propanol, isopropanol, n-butanol, sec-butanol, isobutanol and tert-butanol. Fluorinated $C_1$-$C_4$-alkanols are for example 2-fluoroethanol, 3-fluoropropanol, 1-fluoropropan-2-ol, 4-fluorobutanol, 1,1-difluoroethanol, 2,2-difluoroethanol, 2,2-difluoropropanol, 3,3-difluoropropanol, 1,1-difluoropropan-2-ol, 2,2,2-trifluoroethanol, 3,3,3-trifluoropropanol, 4,4,4-trifluorobutanol and the like. Examples for glycols are ethylene glycol, diethylene glycol and triethylene glycol.

Polar aprotic solvents are polar solvents without a functional group from which a proton can dissociate. Examples for suitable polar aprotic solvents are amides, such as dimethylformamide (DMF), diethylformamide, dibutylformamide, and dimethylacetamide; cyclic ethers, such as tetrahydrofuran, 2-methyltetrahydrofuran, 1,3-dioxane and 1,4-dioxane; sulfoxides, such as dimethylsulfoxide (DMSO); nitriles, such as acetonitrile; lactams, such as N-methylpyrrolidone (NMP), N-(n-butyl)-pyrrolidone or N-(tert-butyl)-pyrrolidone; sulfones, such as sulfolane; carbonic acid esters, such as dimethylcarbonate, ethylenecarbonate or propylene carbonate; lactones, such as γ-butyrolactone or γ-valerolactone; ureas, such as N,N,N',N'-tetramethyl urea, N,N,N',N'-tetrabutyl urea, dimethylpropylene urea (DMPU) or 1,3-dimethyl-2-imidazolinone (DM EU; DMI); and nitro compounds, such as nitromethane.

Examples for suitable $C_1$-$C_4$-alkyl acetates are methyl acetate, ethyl acetate, n-propyl acetate, isopropyl acetate and n-butyl acetate.

Examples for suitable chlorinated alkanes are dichloromethane, trichloromethane or dichloroethane.

Examples for suitable aromatic solvents are benzene, toluene, α,α,α-trifluorotoluene (benzotrifluoride), the xylenes (i.e. 1,2-xylene, 1,3-xylene or 1,4-xylene), fluorobenzene, chlorobenzene, dichlorobenzene or anisole (methoxybenzene).

Examples for suitable heterocyclic solvents are 4-formyl morpholine or dihydrolevoglucosenone (Cyrene®).

If mixtures of the listed organic solvents with water are used, these contain generally up to 15% by weight of water (e.g. 0.5 to 15% by weight), preferably up to 10% by weight of water (e.g. 1 to 10% by weight), in particular up to 5% by weight of water (e.g. 1 to 5% by weight), specifically up to 3% by weight of water of water (e.g. 1 to 3% by weight), relative to the overall weight of the solvent (to be more precise of the mixture of organic solvent and water).

More preferably, the solvent is selected from the group consisting of $C_1$-$C_4$-alkanols, glycols, dimethylformamide, diethylformamide, dibutylformamide, dimethylacetamide, tetrahydrofuran, 2-methyltetrahydrofuran, the dioxanes (i.e. 1,3- and 1,4-dioxane), di-methylsulfoxide, acetonitrile, N-methylpyrrolidone, N-(n-butyl)-pyrrolidone, N-(tert-butyl)-pyrrolidone, sulfolane, dimethylcarbonate, diethylcarbonate, propylene carbonate, γ-valerolactone, N,N,N',N'-tetrabutyl urea, 1,3-dimethyl-2-imidazolinone, ethyl acetate, isopropyl acetate, dichloromethane, trichloromethane, dichloroethane, benzene, toluene, α,α,α-trifluorotoluene, the xylenes, fluorobenzene, chlorobenzene, dichlorobenzene, anisole, 4-formyl morpholine, dihydrolevoglucosenone (Cyrene®), mixtures of the aforementioned solvents, and mixtures of the aforementioned solvents with water; in particular from dimethylformamide, dimethylacetamide, tetrahydrofuran, 2-methyltetrahydrofuran, dimethylsulfoxide, sulfolane, ethyl acetate, ethanol, dichloromethane, trichloromethane, dichloroethane, α,α,α-trifluorotoluene (benzotrifluoride), fluorobenzene, chlorobenzene, dichlorobenzene, anisole (methoxybenzene), and mixtures thereof; and specifically from dimethylformamide, dimethylacetamide and mixtures thereof.

If however formic acid is used as or comprised in the reduction agent and/or a base is used which is liquid at the reaction temperature, the reaction can alternatively be carried out neat.

If a formate is used as only reduction agent, it is expedient to use this in admixture with water. In this case, the solvent comprises preferably also water.

During reaction formic acid or the formate is oxidized to $CO_2$. Given that $CO_2$ inhibits the activity of a number of catalysts, it is expedient to remove $CO_2$ during reaction. This can for example be carried out by sparging an inert gas inert to the reaction through the reaction mixture or by applying a vacuum. Therefore, in a preferred embodiment, during the reaction a gas different from $CO_2$ and which preferably selected from the group consisting of argon, nitrogen, and mixtures of oxygen and nitrogen containing 1-8 vol-% of oxygen, relative to the total amount of the oxygen/nitrogen mixture, is sparged through the reaction mixture; or alternatively or additionally the reaction is carried out under reduced pressure. Specifically, nitrogen is used to remove $CO_2$. The inert gas is typically used at a flow rate of from 1 to 200 l/h, preferably from 1 to 80 l/h, more preferably from 1 to 50 l/h, in particular from 1 to 20 l/h. On industrial scale, the flow rate can of course be distinctly higher, e.g. up to 5000 l/h.

The reaction can be carried out in the presence of an additive which accelerates the reaction rate. Typical additives are diethyl phosphite, borate esters and zinc salts. Suitable zinc salts are for example zinc halides, zinc acetate or zinc trifluoromethanesulfonate. Specifically, diethyl phosphite or a zinc salt, especially zinc acetate, is used. The additive is preferably used in such an amount that the molar ratio of additive and the compound 1 is in the range of from 1:10000 to 10:1, in particular from 1:10000 to 5:1, specifically from 1:10000 to 2:1 e.g. from 1:10000 to 1:2 or 1:10000 to 1:10.

The reaction is carried out at a temperature of preferably from −20 to 120° C. The optimum temperature depends inter alia from the catalyst used. For instance, for some Ru catalysts higher reaction temperatures might be advantageous, so that the reaction temperature in this case can also be in the range of from 30 to 100° C. e.g. from 50 to 90° C., whereas in case of Rh and Ir lower reaction temperatures are sufficient, so that the reaction temperature in this case is preferably in the range of from −20 to 30° C., and in particular from −15 to 25° C. But Ru catalysts also work at temperatures in this range, especially at 10 to 30° C.

The reaction time depends on various factors, such as the reaction temperature, the concentration of the reactants in the reaction mixture and the like. Typically, it is in the range of from about 0 to 48 h, preferably from 1 to 16 h. A reaction time of "0 h" in this context means that after complete addition of all components, the reaction can be sufficiently complete to continue with the isolation of the desired compound (I). This can for example be the case if the addition of the reactants has lasted rather long or if it is intended to recycle the non-reacted starting material.

The reaction is generally carried out by mixing the reduction agent, optionally the base (where in case of the use of formic acid as only reduction agent, mixing with the base is mandatory), the chiral catalyst (either in preformed form or in form of a catalyst precursor and a chiral ligand), optionally the solvent and optionally the additive at the desired reaction temperature or mixing the components and bringing then the temperature to the desired range. The order of addition is not particularly critical. For instance, (i) the reduction agent and optionally the base (in case of formic acid as only reduction agent: mandatorily the base) are added as a mixture or separately (where separate addition can be carried out simultaneously or successively) to a mixture of the compound 1 and the chiral catalyst in a solvent; or (ii) the chiral catalyst in a solvent is added to a mixture of the compound 1, the reduction agent, optionally the base (in case of formic acid as only reduction agent: mandatorily the base) and optionally a solvent (if a formate is used as only reduction agent and no liquid base is used: mandatorily a solvent); or (iii) the reduction agent, optionally in a solvent, is added to a mixture of the compound 1, the chiral catalyst, optionally the base (in case of formic acid as only reduction agent: mandatorily the base) and optionally a solvent (if no liquid base is used: mandatorily a solvent); or (iv) compound 1 in a solvent is added to a mixture of the chiral catalyst, the reduction agent, optionally the base (in case of formic acid as only reduction agent: mandatorily the base) and optionally a solvent (if a formate is used as only reduction agent and no liquid base is used: mandatorily a solvent).

After completion of the reaction, the pyrimidinone of the formula (I) in enantiomerically enriched form is generally isolated from the reaction mixture. Isolation typically comprises adding water to the reaction mixture, isolating and optionally purifying the pyrimidinone of the formula (I) precipitated upon addition of water. Alternatively, and preferably, isolation comprises setting the pH of the reaction mixture acidic; removing at least a part of the solvent, if any, to obtain a concentrate; adding water and a solvent which has low or no miscibility with water to the concentrate; extracting the pyrimidinone of the formula (I) into the solvent which has low or no miscibility with water; and isolating the pyrimidinone of the formula (I) from the extract. The solvent which has low or no miscibility with water is preferably selected from the group consisting of 2-methyltetrahydrofuran, methyl acetate, ethyl acetate, isopropyl acetate, n-butyl acetate, isobutyl acetate, methylisopropyl ketone, and chlorobenzene.

If desired, the catalyst can be recycled. For this purpose, the catalyst is for example recovered either from the reaction mixture obtained after reduction or from one or more of the liquid phases obtained in the workup proceeding after isolation of the pyrimidinone of formula (I) (depending on the solvents used in the reaction and workup, the catalyst can be found in an aqueous phase, an organic phase or both). In one embodiment, only the transition metal is recovered, and not the complete catalyst. The metal can for example be recovered by adsorption on a suitable adsorbent material, such as charcoal or a resin. To this end, the adsorbent material is added to the reaction mixture obtained after reduction or to the one or more of the liquid phases obtained in the workup. On a larger scale, the reaction mixture obtained after reduction or the one or more of the liquid phases obtained in the workup can alternatively be passed once or several times through one or more columns filled with adsorbent. Separation of the metal from the adsorbent can be done by elution (especially when a resin is used), but generally, the adsorbent material is simply burnt. The metal can then be refined and converted into the desired catalyst or catalyst precursor by known methods and used again in the reduction process. Alternatively, the transition metal can be recovered from the liquid phases obtained in the workup which do not contain the compound (I) by removing the solvent of this phase and burning of the remainder. The metal can then be refined and converted into the desired catalyst or catalyst precursor by known methods and used again in the reduction process. If the liquid phase is aqueous, the catalyst is expediently extracted from this into a suitable organic phase, which is then subjected to the described treatment.

The compound 1 is obtainable by reaction of N-methylthiourea with an alkyl 2-phenylmalonate to 6-hydroxy-3-methyl-5-phenyl-2-sulfanyl-pyrimidin-4-one or the corresponding thiolate and reaction thereof with 2-chloro-1-(2-chlorothiazol-5-yl)ethanone to the compound 1. These reactions are described in more detail in EP application no. 21153040.7.

N-methylthiourea and alkyl 2-phenylmalonates are commercially available. 2-Chloro-1-(2-chlorothiazol-5-yl)ethanone can be prepared, for example, as described in WO 2018/197541 or WO 2018/202654 by reaction of 2-chlorothiazole with a Grignard reagent to the corresponding chloro-(2-chlorothiazol-5-yl) magnesium species and reaction thereof with 2-chloro-N-methoxy-N-methyl-acetamide. Alternatively, the compound 3 can be prepared from thiourea according the method described by T. Chalopin et al. in Org. Biomol. Chem., 2016, 14, 3913-3925.

The present method leads to the compound (I) in high yields and high stereoselectivity.

The invention relates moreover to 2-[2-(2-chlorothiazol-5-yl)-2-hydroxy-ethyl]sulfanyl-6-hydroxy-3-methyl-5-phenyl-pyrimidin-4-one (I)

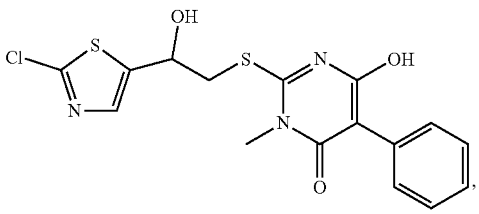 [SMILES: Cn1c(SCC(O)c2cnc(Cl)s2)nc(O)c(-c2ccccc2)c1=O]

, to a tautomer thereof and to enantiomerically enriched forms thereof. This formula (I) and the formula (I) depicted in context with the method of the invention are equivalent; the formula (I) depicted in context with the method of the invention shows however more clearly the stereogenic center of the molecule.

In particular, the invention relates to 2-[(2S)-2-(2-chlorothiazol-5-yl)-2-hydroxy-ethyl]sulfanyl-6-hydroxy-3-methyl-5-phenyl-pyrimidin-4-one of the formula (I-S)

(I-S)

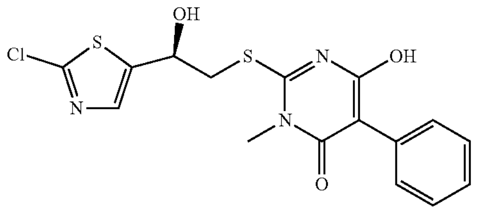

in enantiomeric excess, preferably in an enantiomeric excess of at least 55% ee, more preferably of at least 60% ee, even more preferably of at least 70% ee, in particular of at least 80% ee and specifically of at least 90% ee; and to a tautomer thereof.

In another particular embodiment, the invention relates to 2-[(2R)-2-(2-chlorothiazol-5-yl)-2-hydroxy-ethyl]sulfanyl-6-hydroxy-3-methyl-5-phenyl-pyrimidin-4-one of the formula (I-R)

(I-R)

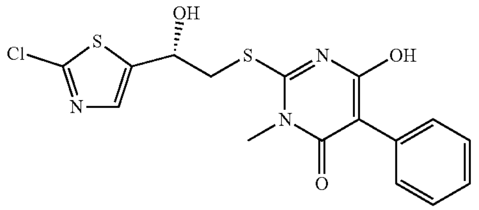

in enantiomeric excess, preferably in an enantiomeric excess of at least 55% ee, more preferably of at least 60% ee, even more preferably of at least 70% ee, in particular of at least 80% ee and specifically of at least 90% ee; and to a tautomer thereof.

The compound (I) can be converted in just one further step into 3-(2-chlorothiazol-5-yl)-8-methyl-7-oxo-6-phenyl-2,3-dihydrothiazolo[3,2-a]pyrimidin-4-ium-5-olate, and especially into enantiomerically enriched forms thereof. For this purpose, the compound (I) is subjected to an internal cyclization by a nucleophilic attack of the unsubstituted nitrogen atom of the pyrimidine ring on the carbon atom carrying the aliphatic OH group. This reaction is described in EP application no. 21153038.1.

The invention relates thus also to the use of 2-[2-(2-chlorothiazol-5-yl)-2-hydroxy-ethyl]sulfanyl-6-hydroxy-3-methyl-5-phenyl-pyrimidin-4-one (I) or of a tautomer thereof or of enantiomerically enriched forms thereof as intermediate in the preparation of 2,3-dihydrothiazolo[3,2-a]pyrimidinium compounds, specifically of 3-(2-chlorothiazol-5-yl)-8-methyl-7-oxo-6-phenyl-2,3-dihydrothiazolo[3,2-a]pyrimidin-4-ium-5-olate and enantiomerically enriched forms thereof.

While the compound (I) can be converted in just one step into 3-(2-chlorothiazol-5-yl)-8-methyl-7-oxo-6-phenyl-2,3- dihydrothiazolo[3,2-a]pyrimidin-4-ium-5-olate and enantiomerically enriched forms thereof, it can also be first subjected to some modifications, such as etherification of the hydroxyl group on the pyrimidine ring, substitution of the Cl atom on the thiazole ring or introduction of substituents on the phenyl ring, so as to allow formation of 2,3-dihydrothiazolo[3,2-a]pyrimidinium compounds other than 3-(2-chlorothiazol-5-yl)-8-methyl-7-oxo-6-phenyl-2,3-dihydrothiazolo[3,2-a]pyrimidin-4-ium-5-olate.

The present invention is further illustrated in the following examples.

EXAMPLES

Abbreviations:

DIPEA diisopropylethylamine
DMAC N,N-dimethylacetamide
DMF N,N-dimethylformamide
DMSO dimethylsulfoxide
EtOAc ethyl acetate
Me-THF 2-methyltetrahydrofuran
THF tetrahydrofuran
TEA triethylamine
TFA trifluoroacetic acid
r.t. room temperature
t time
h hour(s)
min minute(s)
rt retention time

Methods

The compounds were characterized by coupled High Performance Liquid Chromatography/mass spectrometry (H PLC/MS), by NMR or by melting points.

HPLC method: Agilent Eclipse XDB-C18, 150 mm×4.6 mm ID×5 μm

Gradient A=0.5% $H_2SO_4$ in water, B=acetonitrile.

Flow=1.1 mL/min, column oven temperature=30° C.

Gradient program=20% B-100% B–15 min

Run Time=15 min

Chiral HPLC method: Agilent Series 1260, Chiralpak AD-RH 5 μm 150*4.6 mm

Gradient A=0.1% $H_3PO_4$ in water, B=acetonitrile/2-propanol (1:1).

Flow=1.2 mL/min, column oven temperature=50° C.

Gradient program

| t [min] | % B | flow [mL/min] |
|---|---|---|
| 0 | 30 | 1.2 |
| 10 | 50 | 1.2 |
| 15 | 100 | 1.2 |
| 20 | 100 | 1.2 |
| 20.1 | 50 | 1.2 |

Run Time=25 min

LCMS method 1: C18 Column (50 mm×2.1 mm×1.7 μm)

Gradient A=0.1% TFA in water, B=acetonitrile

Flow=0.8 mL/min to 1.0 mL/min in 1.5 min, column oven temperature=60° C.

Gradient program=10% B to 100% B in 15 min, hold for 1 min 100% B, 1 min-10% B

Run time: 1.75 min $^1$H-NMR: The signals are characterized by chemical shift (ppm) vs. tetramethylsilane, by their multiplicity and by their integral (relative number of hydrogen atoms given). The following abbreviations are used to characterize the multiplicity of the signals: m=multiplet, q=quartet, t=triplet, d=doublet, s=singlet, dd=doublet of doublets.

Example 1: Preparation of 2-[(25)-2-(2-chlorothiazol-5-yl)-2-hydroxy-ethyl]sulfanyl-6-hydroxy-3-methyl-5-phenyl-pyrimidin-4-one

1.1 Preparation of 2-[2-(2-chlorothiazol-5-yl)-2-oxo-ethyl]sulfanyl-6-hydroxy-3-methyl-5-phenyl-pyrimidin-4-one In a 20 L jacketed reactor, a solution of N-methylthiourea (778 g, 8.38 mol) and $NaOCH_3$ (1584 g, 8.79 mol, 30 wt % solution in methanol) and methanol (384 g, 12 mol) under $N_2$ was warmed to an internal temperature of 65° C. Then diethyl 2-phenylmalonate (2121 g, 8.79 mol) was dosed over 30 min, and the pump was washed with methanol (384 g, 12 mol). The reaction was then stirred for 4 h at an internal temperature of 65° C., and then for 18 h at 50° C. Over this time a suspension formed. Then a solution of 2-chloro-1-(2-chlorothiazole-5-yl)ethanone (1859 g, 9.00 mol) in ethanol (8.050 g, 175 mol) was dosed over 30 min. The reaction was stirred 75 min at 50° C., and a large precipitation of solid occurred. At this point ethanol (2.300 g, 50 mol) was added, and the stirring speed was increased. The reaction was stirred at 50° C. a further 36 h and then reaction was then cooled to 20° C. over 16 h. The formed solid was then isolated via filtration in three 4 L fritted funnels. Each filtercake was washed with 500 mL of ethanol. The filtercake was then returned to the 20 L reactor and slurried with 15 L of water at 75° C. for 1 h. The slurry was then filtered in two 4 L fritted funnels, and each filtercake washed three times with 500 mL of room temperature water, and then dried at 80° C. and 5 mbar in a vacuum drying oven. After drying 3040 g (91%) of the title compound in form of a brown solid in 99 wt % purity were isolated.

$^1$H NMR (400 MHz, DMSO-d6): δ=8.75 (s, 1H), 7.15-7.45 (m, 5H), 4.9 (s, 2H), 3.46 (s, 3H).

1.2 Preparation of 2-[(2S)-2-(2-chlorothiazol-5-yl)-2-hydroxy-ethyl]sulfanyl-6-hydroxy-3-methyl-5-phenyl-pyrimidin-4-one (I-S)

A solution of 2-[2-(2-chlorothiazol-5-yl)-2-oxo-ethyl]sulfanyl-6-hydroxy-3-methyl-5-phenyl-pyrimidin-4-one (20.0 g, 50.4 mmol, 99% purity, 1.00 eq) and 158.3 g dimethyl acetamide was cooled to −5° C., and a sparge of nitrogen was turned on (dip-tube, 13 Nl/h). 6.0 g of a formic acid (1.54 eq)/diisopropylethylamine (0.375 eq) mixture (molar ratio 4.1:1) were added, followed by a solution of the preformed catalyst Rh(III)ClCp* (1S,2S-TsDPEN) (obtained by reacting $[Rh(III)Cl_2Cp^*]_2$ with 1S,2S-TsDPEN) (0.340 g, 0.501 mmol, 94% purity) in 10 g dimethyl acetamide. The reaction mixture was stirred for 2 h and then $H_2SO_4$ (10 g, 100 mmol, 98% purity) was dosed over 2 h, maintaining an internal temperature <0° C. The pressure on the reactor was reduced to 5 mbar and the temperature on the mantel increased to 57° C. to remove 117 g of dimethyl acetamide via distillation. 178 g of 2-methyltetrahydrofuran and 100 g of water were then added to the reactor. The two phases formed were homogenized for 15 min, and then allowed to separate. The bottom aqueous phase was removed from the reactor. 100 g of water and 2 g $H_2SO_4$ were added to the reactor. The two phases were homogenized for 15 min and then allowed to separate. The bottom aqueous phase and the organic phase were removed separately from the reactor. The combined aqueous phases were returned to the reactor with the addition of 170 g of 2-methyltetrahydrofuran. The two phases were homogenized for 15 min and then allowed to separate. The bottom aqueous phase was removed from the reactor. The 2-methyltetrahydrofuran phases were then returned to the reactor, the pressure was reduced to 350 mbar, and the mantel set at 59° C. to remove water azeotropically via a Dean-Stark trap until <200 ppm water remained in the 2-methyltetrahydrofuran phase. Removal of 2-methyltetrahydrofuran phase gave the title product in 87% yield and 95% ee.

$^1$H NMR (400 MHz, DMSO-d6): δ=11.15 (s, 1H), 7.7 (s, 1H), 7.18-7.47 (m, 5H), 6.5 (s, 1H), 5.2 (m, 1H), 3.72 (dd, 1H), 3.54 (dd, 1H), 3.4 (s, 3H).

Example 2: Preparation of 2-[(2R)-2-(2-chlorothiazol-5-yl)-2-hydroxy-ethyl]sulfanyl-6-hydroxy-3-methyl-5-phenyl-pyrimidin-4-one (I-R) using various reaction conditions The procedure was carried out similarly to example 1.2, using however 1 g of starting compound, DMF (2 ml) as solvent, the catalysts and conditions compiled in the following table, carrying out the reaction at room temperature and quenching the reaction mixture with ethanol. The catalysts were either used in preformed form by reaction of the indicated catalyst precursor and asymmetric ligand or were generated in situ by adding to the reaction mixture the indicated catalyst precursor and asymmetric ligand.

| No. | cat. prec.[1] | asym. lig.[2] | in situ/ pre-formed[3] | amount cat. [mol %][4] | HCOOH:amine[5]; HCOOH amount | Conversion [%] | (I-R) % ee |
|---|---|---|---|---|---|---|---|
| 1 | $[Ir(III)Cl_2Cp^*]_2$ | 1R,2R-TsDPEN | i.s. | 4 | $HC(O)O^-Na^+$/ $H_2O$[6]; 5 eq. | 97 | 90 |
| 2 | $[Ir(III)Cl_2Cp^*]_2$ | 1R,2R-MsDPEN | i.s. | 4 | $HC(O)O^-Na^+$/ $H_2O$[6]; 5 eq. | 95 | 92 |
| 3 | $[Ir(III)Cl_2Cp^*]_2$ | 1R,2R-MsDPEN | i.s. | 2 | 1.1:1; 1.2 eq. | 97 | 90 |
| 4 | $[Ir(III)Cl_2Cp^*]_2$ | 1R,2R-MsDPEN | i.s. | 1 | 1.1:1; 1.2 eq. | 97 | 90 |
| 5 | $[Ir(III)Cl_2Cp^*]_2$ | 1R,2R-MsDPEN | pre. | 1 | 1.1:1; 1.2 eq. | 97 | 90 |
| 6 | $[Ir(III)Cl_2Cp^*]_2$ | 1R,2R-$CF_3$TsDPEN | pre. | 1 | 1.1:1; 1.2 eq. | 91 | 92 |
| 7 | $[Ir(III)Cl_2Cp^*]_2$ | 1R,2R-MeMsDPEN | i.s. | 1 | 1.1:1; 1.2 eq. | 98 | 96 |
| 8 | $[Ir(III)Cl_2Cp^*]_2$ | 1R,2R-MeMsDPEN | pre. | 0.3 | 1.1:1; 1.2 eq. | 99 | 96 |
| 9 | C-3-tethr-RuCl-1R,2R-TsDPEN[7] | | pre. | 4 | 4.5:1; 2.7 eq. | 99 | 90 |
| 10 | $[RuCl_2(mes^8)]_2$ | 1R,2R-TsDPEN | pre. | 4 | 1.1:1; 1.2 eq. | 92 | 82 |
| 11 | $[RuCl_2(mes^8)]_2$ | 1R,2R-TsDPEN | pre. | 2 | 1.1:1; 1.2 eq. | 92 | 80 |
| 12 | $[RuCl_2(cym^9)]_2$ | 1R,2R-MeMsDPEN | pre. | 1 | 1.1:1; 1.2 eq. | 98 | 78 |

[1]cat. prec. = catalyst precursor
[2]asym. lig. = asymmetric ligand
[3]i.s. = catalyst formed in situ (from the indicated catalyst precursor and asymmetric ligand); pre. = catalyst preformed (from the indicated catalyst precursor and asymmetric ligand)
[4]amount of catalyst (calculated as amount of the metal) in mol-%, relative to the amount (in mol) of 2-[2-(2-chlorothiazol-5-yl)-2-oxo-ethyl]sulfanyl-6-hydroxy-3-methyl-5-phenyl-pyrimidin-4-one
[5]molar ratio formic acid: amine. In case that a formate is used instead of formic acid, this is indicated and no molar ratio is given; see [6].
The amount of HCOOH used is given in molar equivalents, relative to the amount (in mol) of 2-[2-(2-chlorothiazol-5-yl)-2-oxo-ethyl]sulfanyl-6-hydroxy-3-methyl-5-phenyl-pyrimidin-4-one used.
[6]instead of formic acid/amine, sodium formate and water (2 ml) were used
[7]C-3-tethr-RuCl-1R,2R-TsDPEN =

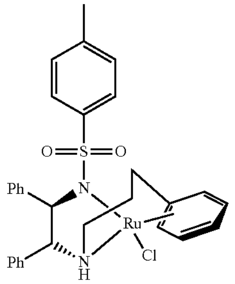

[8]mes = mesitylene
[9]cym = p-cymene

Example 3: Preparation of 2-[(2R)-2-(2-chlorothiazol-5-yl)-2-hydroxy-ethyl]sulfanyl-6-hydroxy-3-methyl-5-phenyl-pyrimidin-4-one using various reaction conditions The procedure was carried out similarly to example 1.2, using however the catalysts and conditions compiled in the following table and carrying out the reaction at 0° C.

| No. | cat. prec.[1] | asym. lig.[2] | in situ/pre-formed[3] | amount cat. [mol %][4] | HCOOH:amine[5]; HCOOH amount | Conversion [%] | (I-R) % ee |
|---|---|---|---|---|---|---|---|
| 13 | $[Ir(III)Cl_2Cp^*]_2$ | 1R,2R-MsDPEN | pre. | 1 | 4.1:1; 1.5 eq. | 100 | 96 |
| 14 | $[Ir(III)Cl_2Cp^*]_2$ | 1R,2R-MeMsDPEN | pre. | 1 | 4.1:1; 1.5 eq. | 100 | 95 |
| 15 | $[Ir(III)Cl_2Cp^*]_2$ | 1R,2R-MeTsDPEN | pre. | 1 | 4.1:1; 1.5 eq. | 95 | 95 |
| 16 | $[Rh(III)Cl_2Cp^*]_2$ | 1R,2R-TsDPEN | pre. | 1 | 4.1:1; 1.5 eq. | 100 | 95 |
| 17 | $[Rh(III)Cl_2Cp^*]_2$ | 1R,2R-MsDPEN | pre. | 1 | 4.1:1; 1.5 eq. | 100 | 95 |

Example 4: Preparation of 2-[(2S)-2-(2-chlorothiazol-5-yl)-2-hydroxy-ethyl]sulfanyl-6-hydroxy-3-methyl-5-phenyl-pyrimidin-4-one (I-S) using various reaction conditions The procedure was carried out analogously to example 1.2, using however the solvents compiled in the following table.

| No. | Solvent | (I-S) % ee |
|---|---|---|
| 18 | DMAC/sulfolane (1:1 v/v) | >95 |
| 19 | DMSO/THF (1:1 v/v) | 91 |
| 20 | DMSO/ethyl acetate (1:1 v/v) | 100 |

Example 5: Preparation of 2-[(2S)-2-(2-chlorothiazol-5-yl)-2-hydroxy-ethyl]sulfanyl-6-hydroxy-3-methyl-5-phenyl-pyrimidin-4-one (I-S) using various reaction conditions The procedure was carried out similarly to example 1.2, using however 400 mg of starting compound and 7 ml of solvent, the solvent, catalyst and conditions being as compiled in the following table. The catalysts were either used in preformed form by reaction of the indicated catalyst precursor and asymmetric ligand or were generated in situ by adding to the reaction mixture the indicated catalyst precursor and asymmetric ligand. The reaction was carried out at room temperature, except for examples 21 and 22 (−5° C.), and for examples 23, 25, 40, 42, 45, 48 and 50 (0° C.).

| No. | cat. [10] | amount cat. [mol %][4] | Solvent | HCOOH:amine[5]; HCOOH amount | Conversion [%] | (I-S) % ee |
|---|---|---|---|---|---|---|
| 21 | 1 | 0.3 | DMAC | 1.75:1; 2.8 eq. | 100 | 97 |
| 22 | 1 | 0.3 | DMAC | 2.8:1; 2.8 eq. | 100 | 97 |
| 23 | 2 | 4 | DMAC | 1.75:1; 2.8 eq. | 100 | 85 |
| 24 | 2 | 2 | DMF | 1.75:1; 2.8 eq. | 100 | 79 |
| 25 | 2 | 4 | DMF | 1.75:1; 2.8 eq. | 100 | 84 |
| 26 | 2 | 4 | benzo-trifluoride | 1.75:1; 2.8 eq. | 100 | n.d. |
| 27 | 2* | 4 | DMAC | 1.75:1; 2.8 eq. | 100 | 80 |
| 28 | 2* | 4 | EtOAc | 1.75:1; 2.8 eq. | 100 | 87 |
| 29 | 2* | 4 | $CHCl_3$ | 1.75:1; 2.8 eq. | 100 | 94 |
| 30 | 2* | 2 | $CHCl_3$ | 1.75:1; 2.8 eq. | 100 | 94 |
| 31 | 2* | 4 | $CH_2Cl_2$ | 1.75:1; 2.8 eq. | 100 | 89 |
| 32 | 2* | 4 | $CH_2Cl_2$ | 1.75:1; 2.8 eq. | 100 | 87 |
| 33 | 2* | 4 | Me-THF | 1.75:1; 2.8 eq. | 98 | 88 |
| 34 | 2* | 4 | dichloro-ethane | 1.75:1; 2.8 eq. | 100 | 86 |
| 35 | 2* | 4 | fluoro-benzene | 1.75:1; 2.8 eq. | 100 | 89 |
| 36 | 2* | 4 | benzo-trifluoride | 1.75:1; 2.8 eq. | 100 | n.d. |
| 37 | 2* | 4 | anisol | 1.75:1; 2.8 eq. | 100 | 98 |
| 38 | 2* | 4 | chloro-benzene | 1.75:1; 2.8 eq. | 100 | 90 |
| 39 | 3 | 4 | $CH_2Cl_2$ | 1.75:1; 2.8 eq. | 100 | 84 |
| 40 | 3 | 4 | $CH_2Cl_2$ | 1.75:1; 2.8 eq. | 100 | 84 |
| 41 | 3 | 2 | $CH_2Cl_2$ | 1.75:1; 2.8 eq. | 100 | 81 |
| 42 | 3 | 4 | DMAC | 1.75:1; 2.8 eq. | 100 | 80 |
| 43 | 4 | 4 | $CHCl_3$ | 1.75:1; 2.8 eq. | 100 | 94 |
| 44 | 4 | 4 | EtOAc | 1.75:1; 2.8 eq. | 91 | 86 |

-continued

| No. | cat. [10] | amount cat. [mol %][4] | Solvent | HCOOH:amine[5]; HCOOH amount | Conversion [%] | (I-S) % ee |
|---|---|---|---|---|---|---|
| 45 | 4 | 4 | $CH_2Cl_2$ | 1.75:1; 2.8 eq. | 100 | 88 |
| 46 | 5 | 4 | $CH_2Cl_2$ | 1.75:1; 2.8 eq. | 100 | 90 |
| 47 | 6 | 4 | $CH_2Cl_2$ | 1.75:1; 2.8 eq. | 100 | 86 |
| 48 | 7 | 4 | dichloro-ethane | 1.75:1; 2.8 eq. | 100 | 93 |
| 49 | 7 | 4 | $CH_2Cl_2$ | 1.75:1; 2.8 eq. | 100 | 95 |
| 50 | 7 | 4 | EtOAc | 1.75:1; 2.8 eq. | 100 | 93 |

[10] catalyst:

Cat. 1: catalyst Rh(III)ClCp* (1S,2S-MsDPEN) of following formula obtained by reacting $[Rh(III)Cl_2Cp^*]_2$ with 1S,2S-MsDPEN:

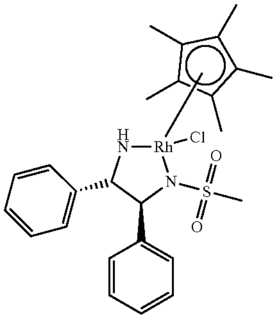

Cat. 2: catalyst RuClMes (1S,2S-TsDPEN) of following formula; preformed; obtained by reacting $[RuCl_2(mes^8)]_2$ with 1S,2S-TsDPEN:

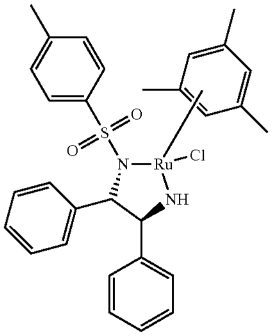

Cat. 2*: like 2, but formed in situ.

Cat. 3: catalyst RuClMes (1S,2S-MsDPEN) of following formula obtained by reacting $[RuCl_2(mes^8)]_2$ with 1S,2S-MsDPEN:

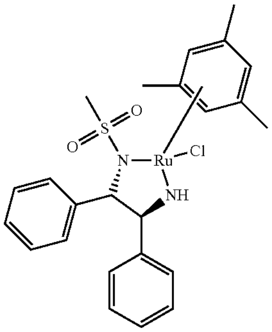

Cat. 4: catalyst RuClMes (1S,2S-CsDPEN) obtained by reacting $[RuCl_2(mes^8)]_2$ with 1S,2S-CsDPEN (to be more precise with N-[(1S,2S)-2-amino-1,2-diphenyl-ethyl]-1-[(1S,4R)-7,7-dimethyl-2-oxo-norbornan-1-yl] methanesulfonamide Cat. 5: catalyst RuClMes (1S,2S-TsDiOMeDPEN) of following formula, obtained by reacting $[RuCl_2(mes^8)]_2$ N-[(1S,2S)-2-amino-1,2-bis(4-methoxyphenyl)ethyl]-4-methyl-benzenesulfonamide:

-continued
| No. cat. [10] | amount cat. [mol %][4] | Solvent | HCOOH:amine[5]; HCOOH amount | Conversion [%] | (I-S) % ee |
|---|---|---|---|---|---|
| 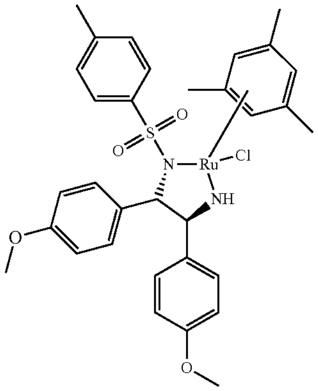 | | | | | |
Cat. 6: catalyst RuClMes (1S,2S-MesitylDPEN) of following formula obtained by reacting $[RuCl_2(mes^8)]_2$ with 1S,2S-MesitylDPEN
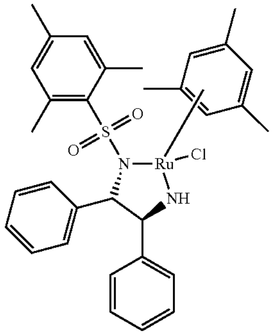
Cat. 7: catalyst RuClMes (1S,2S-RsDPEN) of following formula obtained by reacting $[RuCl_2(mes^8)]_2$ with 1S,2S-RsDPEN
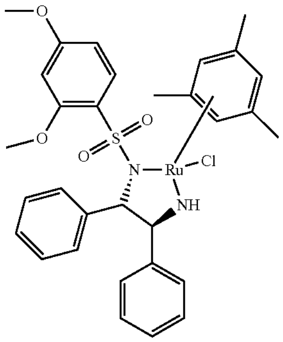

Example 6: Preparation of 2-[(2R)-2-(2-chlorothiazol-5-yl)-2-hydroxy-ethyl]sulfanyl-6-hydroxy-3-methyl-5-phenyl-pyrimidin-4-one (I-R)

The procedure was carried out similarly to example 1.2, using however 4 g (9.93 mmol) of starting compound, ethanol (46 g) as solvent, triethylamine as base (5.98 mmol; 0.6 eq.), 27.09 mmol (2.73 eq.) of formic acid (formic acid:base=4.5:1) and C-3-tethr-RuCl-1R,2R-TsDPEN of the following formula as catalyst (4 mol %)

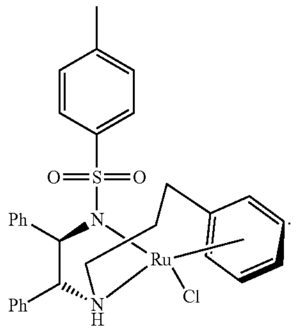

The title product was obtained in 86% yield and 87% ee.

Example 7: Preparation of 2-[(2S)-2-(2-chlorothiazol-5-yl)-2-hydroxy-ethyl]sulfanyl-6-hydroxy-3-methyl-5-phenyl-pyrimidin-4-one (I-S) using various reaction conditions The procedure was carried out similarly to example 1.2, using however the reaction conditions compiled in the following table and carrying out the reaction at −5° C. to 2° C. The solvent was DMAC, except for examples 51 and 67, where DMF was used, and example 70, where DMSO was used. The catalysts were either used in preformed form by reaction of the indicated catalyst precursor and asymmetric ligand or were generated in situ by adding to the reaction mixture the indicated catalyst precursor and asymmetric ligand. Throughout the experiments, (I-S) was obtained with 94-98% ee.

| No. | cat. prec.[1] | asym. lig.[2] | in situ/preformed[3] | amount cat. [mol %][4] | HCOOH:base[5]; HCOOH amount | Conversion [%] |
|---|---|---|---|---|---|---|
| 51 | $[Rh(III)Cl_2Cp^*]_2$ | 1S,2S-TsDPEN | pre. | 0.5 | 1.5:1; 1.2 eq. Base:DIPEA | 86 |
| 52 | $[Rh(III)Cl_2Cp^*]_2$ | 1S,2S-TsDPEN | pre. | 0.3 | 1.5:1; 1.5 eq. Base:DIPEA | 97 |
| 53 | $[Rh(III)Cl_2Cp^*]_2$ | 1S,2S-TsDPEN | pre. | 0.3 | 1.25:1; 1.5 eq. Base:DIPEA | 97 |
| 54 | $[Rh(III)Cl_2Cp^*]_2$ | 1S,2S-TsDPEN | pre. | 0.3 | 1:1; 2 eq. Base:DIPEA | 97 |
| 55 | $[Rh(III)Cl_2Cp^*]_2$ | 1S,2S-TsDPEN | pre. | 0.3 | 1.5:1; 1.5 eq. Base:TEA | 94 |
| 56 | $[Rh(III)Cl_2Cp^*]_2$ | 1S,2S-TsDPEN | i.s. | 0.2 | 1.08:1; 1.3 eq. Base:DIPEA | 95 |
| 57 | $[Rh(III)Cl_2Cp^*]_2$ | 1S,2S-MsDPEN | i.s. | 0.3 | 1.5:1; 1.2 eq. Base:DIPEA | 97 |
| 58 | $[Rh(III)Cl_2Cp^*]_2$ | 1S,2S-MsDPEN | i.s. | 0.3 | 1:1; 1.5 eq. Base:DIPEA | 99 |
| 59 | $[Rh(III)Cl_2Cp^*]_2$ | 1S,2S-MSDPEN | i.s. | 0.2 | 1.5:1; 1.2 eq. Base:DIPEA | 97 |
| 60 | $[Rh(III)Cl_2Cp^*]_2$ | 1S,2S-MsDPEN | i.s. | 0.2 | 1.08:1; 1.3 eq. Base:DIPEA | 97 |
| 61 | $[Rh(III)Cl_2Cp^*]_2$ | 1S,2S-CsDPEN** | i.s. | 0.3 | 1.08:1; 1.3 eq. Base:DIPEA | 97 |
| 62 | $[Rh(III)Cl_2Cp^*]_2$ | 1S,2S-CsDPEN** | i.s. | 0.112 | 1.08:1; 1.3 eq. Base:DIPEA | 94 |
| 63 | $[Rh(III)Cl_2Cp^*]_2$ | 1S,2S-CsDPEN** | i.s. | 0.112 | 1.08:1; 1.3 eq. Base:DIPEA | 95# |
| 64 | $[Rh(III)Cl_2Cp^*]_2$ | 1S,2S-CsDPEN** | i.s. | 0.112 | 1.08:1; 1.3 eq. Base:DIPEA | 98## |
| 65 | $[Rh(III)Cl_2Cp^*]_2$ | 1S,2S-CsDPEN** | i.s. | 0.112 | 1:1; 1.5 eq. Base:DIPEA | 95 |
| 66 | $[Rh(III)Cl_2Cp^*]_2$ | 1S,2S-CsDPEN** | i.s. | 0.15 | 1.6:1; 1.3 eq. Base:DIPEA | 97 |
| 67 | $[Ir(III)Cl_2Cp^*]_2$ | 1S,2S-MeMsDPEN | pre. | 0.5 | 1.5:1; 1.2 eq. Base:DIPEA | 100 |
| 68 | $[Ir(III)Cl_2Cp^*]_2$ | 1S,2S-MeMsDPEN | pre. | 0.5 | 1.5:1; 1.2 eq. Base:DIPEA | 100 |

-continued

| No. | cat. prec.[1] | asym. lig.[2] | in situ/pre-formed[3] | amount cat. [mol %][4] | HCOOH:base[5]; HCOOH amount | Conversion [%] |
|---|---|---|---|---|---|---|
| 69 | $[Ir(III)Cl_2Cp^*]_2$ | 1S,2S-MeMsDPEN | pre. | 0.3 | 3:1; 1.5 eq. Base:KOH | 100 |
| 70 | $[Ir(III)Cl_2Cp^*]_2$ | 1S,2S-MeMsDPEN | pre. | 0.5 | 3:1; 1.5 eq. Base:KOH | 100 |
| 71 | $[Ir(III)Cl_2Cp^*]_2$ | 1S,2S-MeMsDPEN | i.s. | 0.5 | 3.8:1; 1.5 eq. Base:DIPEA | 95 |

**N-[(1S,2S)-2-amino-1,2-diphenyl-ethyl]-1-[(1S,4R)-7,7-dimethyl-2-oxo-norbornan-1-yl]methanesulfonamide

#additionally in the presence of 5 mol % diethyl phosphite additionally in the presence of 0.0125 mol % of zinc acetate. Product obtained with >99% ee.

Example 8: Use of Various Stereoisomers of (1R, 2R)-CsDPEN as Ligand in the Preparation of 2-[(2R)-2-(2-chlorothiazol-5-yl)-2-hydroxy-ethyl]sulfanyl-6-hydroxy-3-methyl-5-phenyl-pyrimidin-4-one (I-R)

To show that the configuration of the camphor moiety of the CsDPEN ligand has essentially no influence on the stereoselectivity in the reaction of 2-[2-(2-chlorothiazol-5-yl)-2-oxo-ethyl]sulfanyl-6-hydroxy-3-methyl-5-phenyl-pyrimidin-4-one 1 to the product (I), hydrogenation was carried out with two different (1R,2R)-CsDPEN stereoisomers, namely with N-[(1R,2R)-2-amino-1,2-diphenyl-ethyl]-1-[(1S,4R)-7,7-dimethyl-2-oxo-norbornan-1-yl]methanesulfonamide) and with N-[(1R,2R)-2-amino-1,2-diphenyl-ethyl]-1-[(1R,4S)-7,7-dimethyl-2-oxo-norbornan-1-yl]methanesulfonamide) The reaction was carried out similarly to example 1.2, using DMAC as solvent, 1.2 eq. of formic acid, 0.8 eq. of diisopropylethylamine as base and 0.2 mol % of the catalyst RhClCp* (1R,2R-CsDPEN-1) (formed in situ by mixing $[Rh(III)Cl_2Cp^*]_2$, N-[(1R,2R)-2-amino-1,2-diphenyl-ethyl]-1-[(1S,4R)-7,7-dimethyl-2-oxo-norbornan-1-yl]methanesulfonamide and diisopropylethylamine used in a molar ratio of 1:3:7) or 0.2 mol % of the catalyst RhClCp*(1R,2R-CsDPEN-2) (formed in situ by mixing $[Rh(III)Cl_2Cp^*]_2$, N-[(1R,2R)-2-amino-1,2-diphenyl-ethyl]-1-[(1R,4S)-7,7-dimethyl-2-oxo-norbornan-1-yl]methanesulfonamide and diisopropylethylamine used in a molar ratio of 1:3:7). The reaction was carried out at −5° C.

The reaction in which RhClCp* (1R,2R-CsDPEN-1) was used as catalyst yielded (I-R) in an enantiomeric purity of 97% ee (conversion: 95%); the reaction in which RhClCp* (1R,2R-CsDPEN-2) was used as catalyst yielded (I-R) in an enantiomeric purity of 98% ee (conversion: 98%).

The invention claimed is:

1. A method for preparing an enantiomerically enriched form of 2-[2-(2-chlorothiazol-5-yl)-2-hydroxy-ethyl]sulfanyl-6-hydroxy-3-methyl-5-phenyl-pyrimidin-4-one of formula (I):

(I)

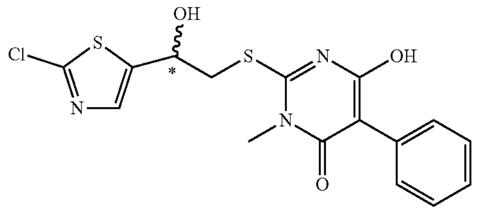

where the asterisk * shows a stereogenic center; or of a tautomer thereof;

which method comprises reducing 2-[2-(2-chlorothiazol-5-yl)-2-oxo-ethyl]sulfanyl-6-hydroxy-3-methyl-5-phenyl-pyrimidin-4-one of formula 1

1

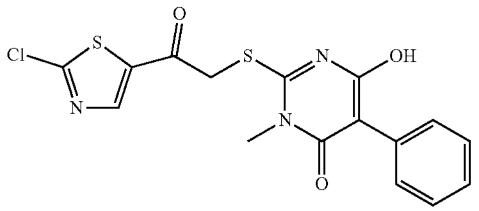

or a tautomer thereof with a reduction agent selected from the group consisting of formic acid HC(═O)OH, formates of the formula HC(═O) O $M^+$, and mixtures of formic acid HC(═O)OH and one or more formates of the formula HC(═O)$O^-M^+$, where $M^+$ is a cation equivalent; in the presence of a chiral transition metal catalyst and optionally a base, where in the case that formic acid is used as reduction agent, the reaction is carried out in the presence of a base;

to obtain an enantiomerically enriched form of the pyrimidinone of the formula (I) or of a tautomer thereof.

2. The method according to claim 1, where $M^+$ is selected from the group consisting of alkali metal cations, ammonium cations of the formula $[NHR^1R^2R^3]^+$, where $R^1$, $R^2$, and $R^3$, independently of each other, are selected from the group consisting of hydrogen, $C_1$-$C_6$-alkyl, $C_3$-$C_6$-cycloalkyl, $C_1$-$C_4$-alkoxy, and $C_1$-$C_4$-alkoxy-$C_1$-$C_4$-alkyl, protonated diamines of the formula $NR^1R^2$-A-$NR^3R^4$, where $R^1$, $R^2$, $R^3$, and $R^4$, independently of each other, are selected from the group consisting of hydrogen, $C_1$-$C_6$-alkyl, $C_3$-$C_6$-cycloalkyl, $C_1$-$C_4$-alkoxy, and $C_1$-$C_4$-alkoxy-$C_1$-$C_4$-alkyl, and A is $(CH_2)_2$ or $(CH_2)_3$; and protonated 5- or 6-membered saturated heterocyclic rings containing one nitrogen atom as ring member and optionally one further heteroatom selected from N and O as ring member, where the ring may carry 1 to 6 $C_1$-$C_4$-alkyl groups and/or 1 or 2 OH groups.

3. The method according to claim 1, where the base is selected from the group consisting of alkali metal hydroxides, amines of the formula $NR^1R^2R^3$, where $R^1$, $R^2$, and $R^3$, independently of each other, are selected from the group consisting of hydrogen, $C_1$-$C_6$-alkyl, $C_3$-$C_6$-cycloalkyl, $C_1$-$C_4$-alkoxy, and $C_1$-$C_4$-alkoxy-$C_1$-$C_4$-alkyl, where at least one of $R^1$, $R^2$, and $R^3$ is not hydrogen; diamines of the formula $NR^1R^2$-A-$NR^3R^4$, where $R^1$, $R^2$, $R^3$, and $R^4$, independently of each other, are selected from the group consisting of hydrogen, $C_1$-$C_6$-alkyl, $C_3$-$C_6$-cycloalkyl, $C_1$-$C_4$- alkoxy, and $C_1$-$C_4$-alkoxy-$C_1$-$C_4$-alkyl, and A is ($CH_2$) 2 or ($CH_2$) 3; and a 5- or 6-membered saturated heterocyclic ring containing one nitrogen atom as ring member and optionally one further heteroatom selected from N and O as ring member, where the ring may carry 1 to 6 $C_1$-$C_4$-alkyl groups and/or 1 or 2 OH groups, where the bases can be used in supported from.

4. The method according to claim 1, where the formic acid is used as reduction agent, where the formic acid and the base are used in a molar ratio of from 100:1 to 1:10.

5. The method according to claim 1, where the chiral transition metal catalyst is selected from group VIII metal catalysts.

6. The method according to claim 5, where the chiral transition metal catalyst is selected from Ru, Rh, and Ir catalysts.

7. The method according to claim 1, where the chiral transition metal catalyst, calculated on the basis of the transition metal content, is used in an amount of 0.01 to 10 mol % relative to 1 mol of the compound of formula 1.

8. The method according to claim 7, where the chiral transition metal catalyst, calculated on the basis of the transition metal content, is used in an amount of 0.1 to 5 mol-% relative to 1 mol of the compound of formula 1.

9. The method according to claim 1, where the chiral transition metal catalyst is either preformed and contains one or more chiral ligands coordinated to a transition metal; or is formed in situ by reaction of a transition metal precursor compound and one or more chiral ligands.

10. The method according to claim 1, where the chiral transition metal catalyst comprises one or more chiral ligands coordinated to a transition metal, where the chiral ligands are selected from the group consisting of bidentate amine-based chiral ligands.

11. The method according to claim 10, where the chiral transition metal catalyst comprises one or more chiral ligands coordinated to a transition metal, where the chiral ligands are selected from the group consisting of chiral forms of 1,2-diphenyl-ethylene-1,2-diamines of formula (II)

(II)

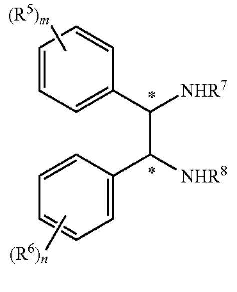

where the asterisk shows the stereogenic centers;

$R^5$ and $R^6$, independently of each other, are selected from the group consisting of OH, halogen, $C_1$-$C_4$-alkyl, and $C_1$-$C_4$-alkoxy;

$R^7$ and $R^8$, independently of each other, are selected from the group consisting of hydrogen, $C_1$-$C_4$-alkyl, -L-phenyl, where the phenyl ring may carry 1, 2, 3, 4, or 5 substituents selected from the group consisting of $C_1$-$C_4$-alkyl, $C_1$-$C_4$-haloalkyl, and $C_1$-$C_4$-alkoxy; and $SO_2R^9$;

L is a linker selected from the group consisting of $C_2$-$C_6$-alkylene, $C_1$-$C_3$-alkylene-O—$(CH_2)_p$, where p is 0, 1, or 2; and $C_1$-$C_3$-alkylene-(1,2-phenylene)-$(CH_2)_r$, where r is 0, 1, or 2;

$R^9$ is selected from the group consisting of $C_1$-$C_4$-alkyl, $C_1$-$C_4$-haloalkyl, phenyl, phenyl-$C_1$-$C_3$-alkyl, where phenyl in the two aforementioned radicals optionally carry 1, 2, 3, 4, or 5 substituents selected from the group consisting of halogen, $C_1$-$C_4$-alkyl, $C_1$-$C_4$-haloalkyl, and $C_1$-$C_4$-alkoxy; naphthyl, and $NR^{10}R^{11}$;

$R^{10}$ is hydrogen or $C_1$-$C_4$-alkyl;

$R^{11}$ is phenyl-$C_1$-$C_3$-alkyl, where the phenyl ring may carry 1, 2, 3, 4, or 5 substituents selected from the group consisting of halogen, $C_1$-$C_4$-alkyl, $C_1$-$C_4$-haloalkyl, and $C_1$-$C_4$-alkoxy; and m and n, independently of each other, are 0, 1, 2, 3, 4, or 5.

12. The method according to claim 11, where the chiral transition metal catalyst comprises one or more chiral ligands coordinated to a transition metal, where the chiral ligands are selected from the group consisting of (1R,2R) or (1S,2S) forms of DPEN, TSDPEN, $CF_3$TsDPEN, MsDPEN, MeMsDPEN, MeTsDPEN, FsDPEN, TripsMesitylDPEN, CsDPEN, MesitylDPEN, RsDPEN, TsDiOMeDPEN, and the compound of formula (II), wherein $R^7$ is $SO_2R^9$, where $R^9$ is $C_1$-$C_4$-alkyl or phenyl which optionally carry 1, 2, or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals optionally carry 1, 2, or 3 substituents selected from the group consisting of $C_1$-$C_4$-alkyl, $C_1$-$C_4$-haloalkyl, and $C_1$-$C_4$-alkoxy; and m and n are 0.

13. The method according to claim 12, where the chiral transition metal catalyst is selected from catalysts containing Ru, Rh, or Ir as central metal and at least one ligand selected from the group consisting of the (1R,2R) or (1S,2S) forms of DPEN, TsDPEN, $CF_3$TsDPEN, MsDPEN, MeMsDPEN, MeTsDPEN, FsDPEN, TripsMesitylDPEN, CsDPEN, MesitylDPEN, RsDPEN, and TsDiOMeDPEN; and from catalysts containing Ru as central metal and at least one ligand selected from the (1R,2R) or (1S,2S) forms of the compound of formula (II), wherein $R^7$ is $SO_2R^9$, where $R^9$ is $C_1$-$C_4$-alkyl or phenyl which optionally carry 1, 2, or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals optionally carry 1, 2, or 3 substituents selected from the group consisting of $C_1$-$C_4$-alkyl, $C_1$-$C_4$-haloalkyl and $C_1$-$C_4$-alkoxy; and m and n are 0.

14. The method according to claim 11, where in the case that none of $R^7$ and $R^8$ is -L-phenyl or $SO_2R^9$ with $R^9$ being phenyl-$C_1$-$C_3$-alkyl or $NR^{10}R^{11}$, the catalyst contains additionally a ligand selected from Cp, Cp*, benzene, p-cymene, mesitylene and hexamethylbenzene.

15. The method according to claim 11, for preparing 2-sulfanyl-6-hydroxy-3-methyl-5-phenyl-pyrimidin-4-one of formula (I-S)

(I-S)

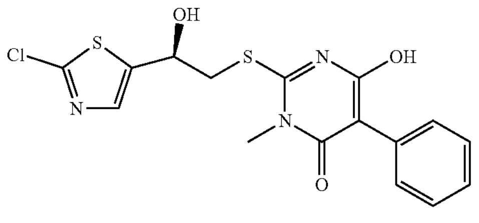

or a tautomer thereof in an enantiomeric excess of at least 55% ee, where a chiral transition metal catalyst used comprises a chiral ligand selected from the group consisting of (1S,2S)-DPEN, (1S,2S)-TsDPEN, (1S,2S)-$CF_3$TsDPEN, (1S,2S)-MsDPEN, (1S,2S)-MeMsDPEN, (1S,2S)-MeTsDPEN, (1S,2S)-FsDPEN, (1S,2S)-TripsMesitylDPEN, (1S,2S)-CsDPEN, (1S,2S)-MesitylDPEN, (1S,2S)-RsDPEN, (1S,2S)-TsDiOMeDPEN, and the (1S,2S) form of a compound of the formula (II), wherein $R^7$ is $SO_2R^9$, where $R^9$ is $C_1$-$C_4$-alkyl or phenyl which optionally carry 1, 2, or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals optionally carry 1, 2, or 3 substituents selected from the group consisting of $C_1$-$C_4$-alkyl, $C_1$-$C_4$-haloalkyl, and $C_1$-$C_4$-alkoxy; and m and n are 0;

or for preparing 2-sulfanyl-6-hydroxy-3-methyl-5-phenyl-pyrimidin-4-one of formula (I-R)

(I-R)

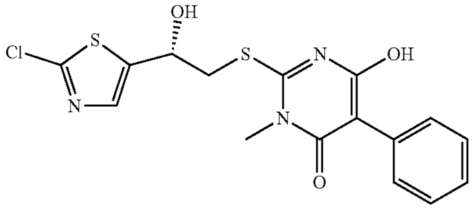

or a tautomer thereof in an enantiomeric excess of at least 55% ee, where the chiral transition metal catalyst used comprises a chiral ligand selected from the group consisting of (1R,2R)-DPEN, (1R,2R)-TsDPEN, (1R,2R)-$CF_3$TsDPEN, (1R,2R)-MsDPEN, (1R,2R)-MeMsDPEN, (1R,2R)-MeTsDPEN, (1R,2R)-FsDPEN, (1R,2R)-TripsMesitylDPEN, (1R,2R)-CsDPEN, (1R,2R)-MesitylDPEN, (1R,2R)-RsDPEN, (1R,2R)-TsDiOMeDPEN, and the (1R,2R) form of the compound of formula (II), wherein $R^7$ is $SO_2R^9$, where $R^9$ is $C_1$-$C_4$-alkyl or phenyl which optionally carry 1, 2, or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals optionally carry 1, 2, or 3 substituents selected from the group consisting of $C_1$-$C_4$-alkyl, $C_1$-$C_4$-haloalkyl, and $C_1$-$C_4$-alkoxy; and m and n are 0.

16. The method according to claim 15, for preparing 2-sulfanyl-6-hydroxy-3-methyl-5-phenyl-pyrimidin-4-one of the formula (I-S) or a tautomer thereof in an enantiomeric excess of at least 70% ee, where the chiral transition metal catalyst comprises as central metal Ru, Rh, or Ir, and comprises a chiral ligand selected from the group consisting of (1S,2S)-DPEN, (1S,2S)-TsDPEN, (1S,2S)-$CF_3$TsDPEN, (1S,2S)-MsDPEN, (1S,2S)-MeMsDPEN, (1S,2S)-MeTsDPEN, (1S,2S)-FsDPEN, (1S,2S)-TripsMesitylDPEN, (1S,2S)-CsDPEN, (1S,2S)-MesitylDPEN, (1S,2S)-RsDPEN, and (1S,2S)-TsDiOMeDPEN; or is a catalyst containing Ru as central metal and at least one ligand selected from the (1S,2S) form of the compound of formula (II), wherein $R^7$ is $SO_2R^9$, where $R^9$ is $C_1$-$C_4$-alkyl or phenyl which optionally carry 1, 2, or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals optionally carry 1, 2, or 3 substituents selected from the group consisting of $C_1$-$C_4$-alkyl, $C_1$-$C_4$-haloalkyl, and $C_1$-$C_4$-alkoxy; and m and n are 0;

or for preparing 2-sulfanyl-6-hydroxy-3-methyl-5-phenyl-pyrimidin-4-one of the formula (I-R) or a tautomer thereof in an enantiomeric excess of at least 70% ee, where the chiral transition metal catalyst comprises as central metal Ru, Rh, or Ir, and comprises a chiral ligand selected from the group consisting of (1R,2R)-DPEN, (1R,2R)-TsDPEN, (1R,2R)-$CF_3$TsDPEN, (1R,2R)-MsDPEN, (1R,2R)-MeMsDPEN, (1R,2R)-MeTsDPEN, (1R,2R)-FsDPEN, (1R,2R)-TripsMesitylDPEN, (1R,2R)-CsDPEN, (1R,2R)-MesitylDPEN, (1R,2R)-RsDPEN, and (1R,2R)-TsDiOMeDPEN; or is a catalyst containing Ru as central metal and at least one ligand selected from the (1R,2R) form of the compound of formula (II), wherein $R^7$ is $SO_2R^9$, where $R^9$ is $C_1$-$C_4$-alkyl or phenyl which optionally carry 1, 2, or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals optionally carry 1, 2, or 3 substituents selected from the group consisting of $C_1$-$C_4$-alkyl, $C_1$-$C_4$-haloalkyl, and $C_1$-$C_4$-alkoxy; and m and n are 0.

17. The method according to claim 1, where during the reaction a gas different from $CO_2$ is sparged through the reaction mixture; or where alternatively or additionally the reaction is carried out under reduced pressure.

18. The method according claim 1, where the reaction is carried out in the presence of an additive selected from the group consisting of diethyl phosphite, borate esters, and zinc salts; where the additive is used in an amount such that a molar ratio of the additive and the compound of formula 1 is in a range of from 1:10000 to 10:1.

19. 2-sulfanyl-6-hydroxy-3-methyl-5-phenyl-pyrimidin-4-one of the formula (I) or an enatiomerically enriched form thereof (I)

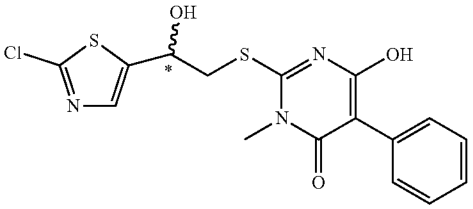

where the asterisk * shows the stereogenic center; or a tautomer thereof.

20. The method according to claim 2 where $M^+$ is selected from the group consisting of $Li^+$, $Na^+$, $K^+$, $Cs^+$, $NH_4^+$, $[NH_2(C_2H_5)_2]^+$, $[NH(C_2H_5)_3]^+$, $[NH(CH_2CH_2CH_2CH_3)_3]^+$, $[NH(C_2H_5)(CH(CH_3)_2]^+$, $[NH(CH_3)_2(CH(CH_3)]^+$, $[NH_2(C_2H_5)(C(CH_3)_3]^+$, $[NH_2(CH(CH_3)_2)(C(CH_3)_3]^+$, $[NH_2(C_2H_4OCH_3)(CH_3)]^+$, $[NH(cyclohexyl)_2(CH_3)]^+$, $[NH(cyclohexyl)(CH_3)_2]^+$, protonated N,N,N',N'-tetramethylethylenediamine, protonated N,N,N',N'-tetramethylpropylene-1,3-diamine, protonated piperdine, protonated N-methylpiperidine, protonated 2,2,6,6-tetramethylpiperidine, protonated N-methyl-2,6,6-tetramethylpiperidine, protonated N-methyl-4-hydroxy-2,2,6,6-tetramethylpiperidine, protonated morpholine, and protonated N-methylmorpholine.

21. The method according to claim 3 where the base is selected from the group consisting of LiOH, NaOH, KOH, diethylamine, triethylamine, tributylamine, diisopropylethylamine, dimethylisopropylamine, ethyl-tert-butylamine, isopropyl-tert-butylamine, (2-methoxyethyl)methylamine, N,N-dicyclohexylmethylamine, N-cyclohexyldimethylamine, N,N,N',N'-tetramethylethylenediamine, N,N,N',N'-tetramethylpropylene-1,3-diamine, piperdine, N-methylpiperidine, 2,2,6,6-tetramethylpiperidine, N-methyl-2,6,6-tetramethylpiperidine, N-methyl-4-hydroxy-2,2,6,6-tetramethylpiperidine, morpholine, and N-methylmorpholine.

22. The method according to claim 10 where the chiral ligands are selected from the group consisting of chiral 1,2-diphenyl-ethylene-1,2-diamines, 1,2-cyclohexanediamines, and 1,2-bis(methylamino)cyclohexanes.

23. The method according to claim 12 where the chiral transition metal catalyst is selected from catalysts containing Ru, Rh, or Ir as central metal and at least one chiral ligand selected from the group consisting of the (1R,2R) or (1S,2S) forms of DPEN, TSDPEN, $CF_3$TSDPEN, MsDPEN, MeMsDPEN, MeTsDPEN, FsDPEN, TripsMesitylDPEN, CsDPEN, MesitylDPEN, RsDPEN, TsDiOMeDPEN, and the compound of formula (II), wherein $R^7$ is $SO_2R^9$, where $R^9$ is $C_1$-$C_4$-alkyl or phenyl which optionally carry 1, 2, or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals optionally carry 1, 2, or 3 substituents selected from the group consisting of $C_1$-$C_4$-alkyl, $C_1$-$C_4$-haloalkyl, and $C_1$-$C_4$-alkoxy; and m and n are 0.

24. The method according to claim 13 where the chiral transition metal catalyst is selected from catalysts containing Ru, Rh, or Ir as central metal and at least one ligand selected from the group consisting of the (1R,2R) or (1S,2S) forms of TsDPEN, $CF_3$TsDPEN, MsDPEN, MeMsDPEN, MeTsDPEN, CsDPEN, MesitylDPEN, RsDPEN, and TsDiOMeDPEN; and from catalysts containing Ru as central metal and at least one ligand selected from the (1R,2R) or (1S,2S) forms of the compound of the formula (II), wherein $R^7$ is $SO_2R^9$, where $R^9$ is $C_1$-$C_4$-alkyl or phenyl which optionally carry 1, 2, or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl; and m and n are 0.

25. The method according to claim 15 where the chiral transition metal catalyst comprises as central metal Ru, Rh, or Ir, and comprises a chiral ligand selected from the group consisting of (1S,2S)-DPEN, (1S,2S)-TsDPEN, (1S,2S)-$CF_3$TsDPEN, (1S,2S)-MsDPEN, (1S,2S)-MeMsDPEN, (1S,2S)-MeTsDPEN, (1S,2S)-FsDPEN, (1S,2S)-TripsMesitylDPEN, (1S,2S)-CsDPEN, (1S,2S)-MesitylDPEN, (1S,2S)-RsDPEN, (1S,2S)-TsDiOMeDPEN, and the (1S,2S) form of the compound of formula (II), wherein $R^7$ is $SO_2R^9$, where $R^9$ is $C_1$-$C_4$-alkyl or phenyl which optionally carry 1, 2, or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals optionally carry 1, 2, or 3 substituents selected from the group consisting of $C_1$-$C_4$-alkyl, $C_1$-$C_4$-haloalkyl, and $C_1$-$C_4$-alkoxy; and m and n are 0.

26. The method according to claim 16 where the chiral transition metal catalyst comprises as central metal Ru, Rh, or Ir, and comprises a chiral ligand selected from the group consisting of (1S,2S)-TsDPEN, (1S,2S)-$CF_3$TsDPEN, (1S,2S)-MsDPEN, (1S,2S)-MeMsDPEN, (1S,2S)-MeTsDPEN, (1S,2S)-CsDPEN, (1S,2S)-MesitylDPEN, (1S,2S)-RsDPEN, and (1S,2S)-TsDiOMeDPEN; or is a catalyst containing Ru as central metal and at least one ligand selected from the (1S,2S) form of the compound of formula (II), wherein $R^7$ is $SO_2R^9$, where $R^9$ is $C_1$-$C_4$-alkyl or phenyl which optionally carry 1, 2, or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl; and m and n are 0.

* * * * *